US005604301A

United States Patent [19]

Mountford et al.

[11] Patent Number: 5,604,301
[45] Date of Patent: Feb. 18, 1997

[54] ULTRASOUND DETECTION TECHNIQUES

[76] Inventors: Norman D. G. Mountford, 39 Richview Road, Islington, Ontario, Canada, M9A 4M7; Iain D. Sommerville, 2063 Seafare Drive, Oakville, Ontario, Canada, L6L 1P5

[21] Appl. No.: 413,725

[22] Filed: Mar. 31, 1995

Related U.S. Application Data

[63] Continuation-in-part of Ser. No. 971,536, Nov. 4, 1992, abandoned, which is a continuation-in-part of Ser. No. 864,450, Apr. 6, 1992, abandoned.

[51] Int. Cl.$^6$ .................................................. G01N 29/02
[52] U.S. Cl. .................................. 73/61.75; 73/865.5
[58] Field of Search .......................... 73/61.42, 61.75, 73/617, 627, 628, 865.5, 19.03, 19.1, 24.03, 620, 624

[56] References Cited

U.S. PATENT DOCUMENTS

| | | | |
|---|---|---|---|
| 3,444,726 | 5/1969 | Young et al. | 73/61.75 |
| 4,112,735 | 9/1978 | McKnight | 73/865.5 X |
| 5,125,514 | 6/1992 | Oehler et al. | 73/627 X |

FOREIGN PATENT DOCUMENTS

| | | | |
|---|---|---|---|
| 2257786 | 1/1993 | United Kingdom | 73/61.45 |

*Primary Examiner*—Michael Brock
*Attorney, Agent, or Firm*—Fitzpatrick, Cella, Harper & Scinto

[57] ABSTRACT

A method for separating a liquid and in particular a liquid metal from heterogeneous constituents therein, comprises the steps of providing a passage for a flow of liquid containing heterogeneous constituents and directing ultrasound waves into the passage. The ultrasound waves are made to form standing waves in the liquid using a reflector and by tuning the frequency of the ultrasound waves. The standing waves cause extraneous particles in the liquid to coagulate at the nodes. The reflector is also designed to direct some of the ultrasound waves upwardly into the passage. The flow of the liquid metal through the passage and the ultrasound in the passage carry the coagulated particles into the slag on the surface of the liquid metal for removal. The ultrasound waves also cause cavitation effects which degas the liquid metal. An ultrasound particle detection device is also disclosed which includes a transmitting delay line, a receiving delay line and a reflector immersed in a liquid. The reflector reflects ultrasound from the transmitting delay line to a focal volume. The receiving delay line receives ultrasound reflected by extraneous particles in the focal volume allowing for their detection.

11 Claims, 18 Drawing Sheets

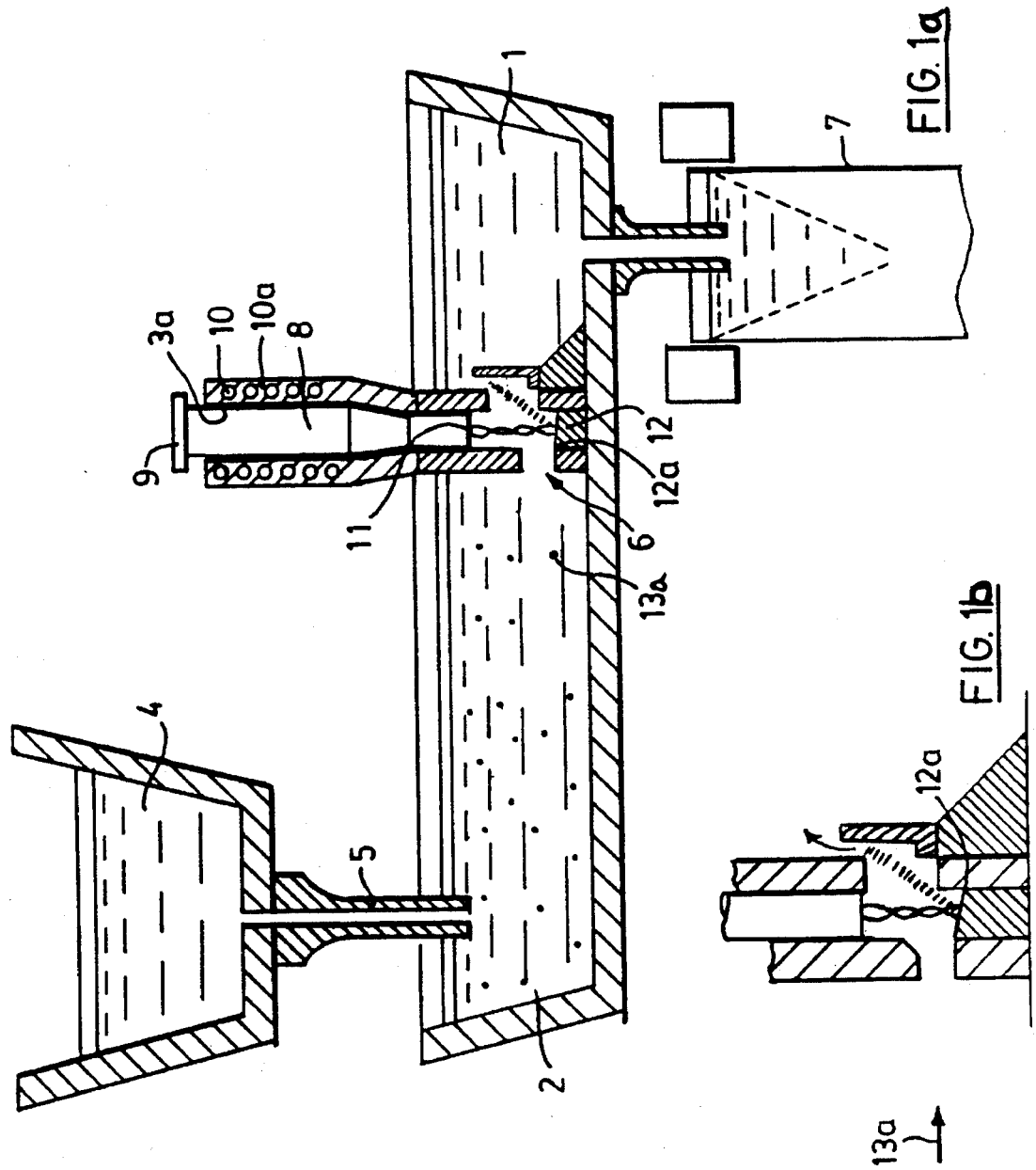

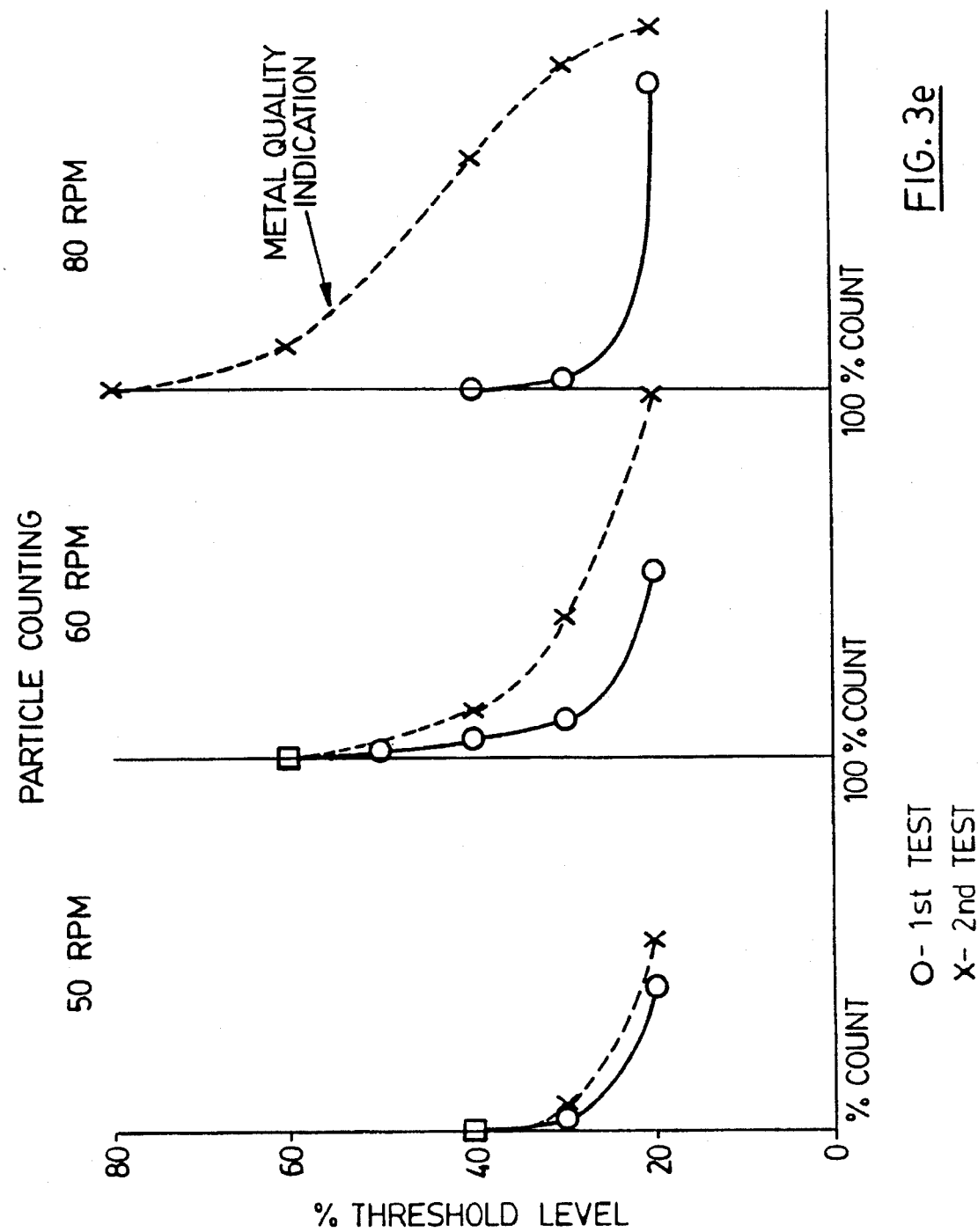

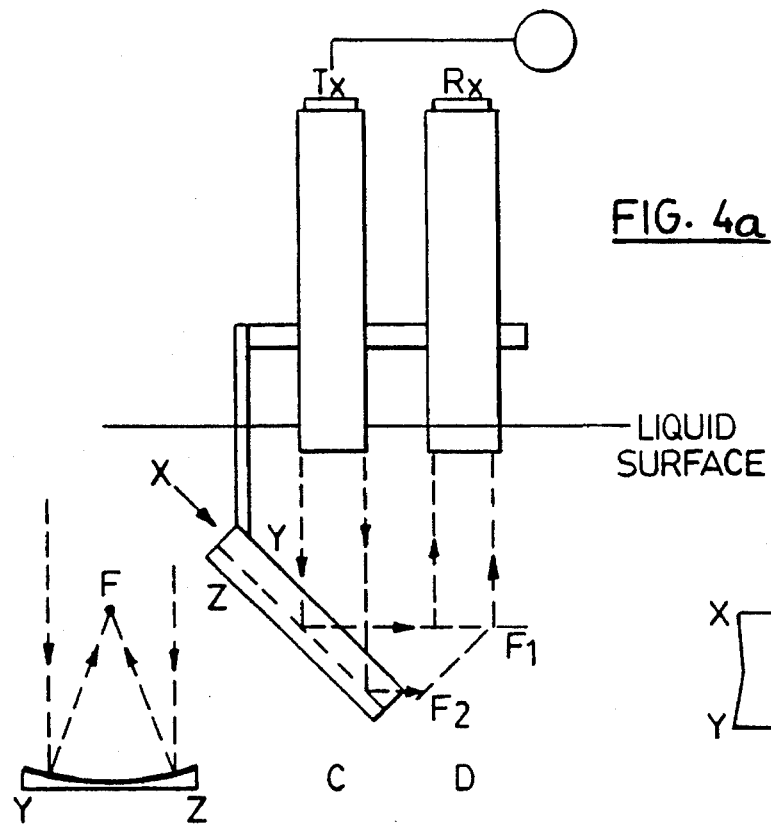
FIG. 4a
FIG. 4b
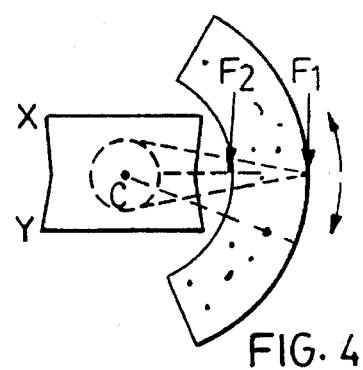
FIG. 4c
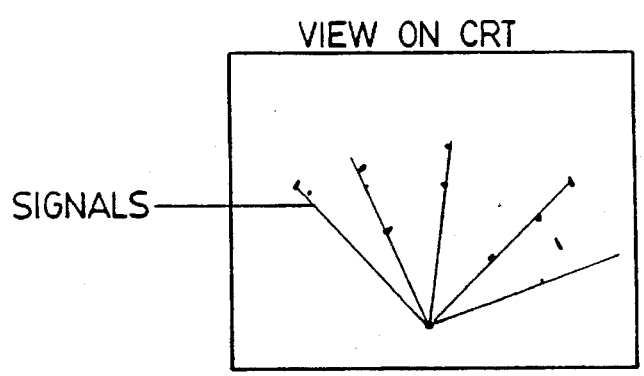
FIG. 4d

| N | ZONE OF MINIMUM ENERGY CHANGE. |
|---|---|
| T --- | ZONE OF MAXIMUM TENSION FORCES. |
| C --- | ZONE OF MAXIMUM COMPRESSION FORCES. |

# 5,604,301

ULTRASOUND DETECTION TECHNIQUES

RELATED APPLICATIONS

This is a continuation-in-part of U.S. application Ser. No. 07/971,536 filed on Nov. 4, 1992, now abandoned, which is a continuation-in-part of U.S. application Ser. No. 07/864,450 filed on Apr. 6, 1992 now abandoned.

FIELD OF THE INVENTION

The present invention relates to improvements in the transmission of ultrasound through liquids for the purpose of treatment for impurities therein and the measuring of certain characteristics relating thereto.

BACKGROUND OF THE INVENTION

Many liquids from aqueous solution to liquid metals such as steel may contain impurities which end up in the solid and affect the purpose for which they are used. For example, aqueous solutions as by-products from mineral dressing processes may contain a residue of fine particles in excess of that allowed. The effluent from a sewage works, for example, may be in excess of such levels thought to be safe for drinking purposes.

In many of these aqueous processes a simple filtration process can be used in order to obtain a cleaner residue. In other cases, such as those with high temperatures, for example aluminum melts, it is possible to use relatively coarse forms of filter material. These take the form of beds of alumina balls graded in size from top to bottom with filter depths on the order of 100–150 centimeters. These filters are capable of filtering out the entrained oxide created by turbulent metal transfer and also the fine but very hard particles such as the TiC (titanium carbide) derived from the electrolytic recovery process. However, problems exist in that filters only last until they are saturated with oxides and other particles and when this occurs, the rate of metal flow through them decreases. Moreover, any movement of the filter can send quantities of extraneous material down a launder and contaminate a large quantity of metal.

Magnesium is also prone to pick up this form of oxide contamination and in the case of aluminum bronze such contaminates are an accepted hazard.

In the case of ferrous alloys, the contaminants are derived from re-oxidation during metal transfer and from the addition of 'killing' elements such as aluminum and silicon used to counteract this re-oxidation of the melt. The by-products of these reactions are oxides of silicon and aluminum. The former will be in the form of complex, liquid silicates which form long stringers in the final products and in the latter case hard crystalline alumina particles, which again cause problems during casting, such as blockage of the nozzles through which the steel is conveyed from the ladle to the tundish. Particles also aggregate into large clusters which have a deleterious effect on metal properties.

It is therefore an object of the present invention to obviate or mitigate at least some of the above-mentioned disadvantages.

SUMMARY OF THE INVENTION

According to one aspect of the present invention there is provided a method for separating a liquid metal from heterogeneous constituents therein, comprising the steps of:

i) providing a passage for a flow of liquid metal containing heterogeneous constituents; and ii) directing ultrasound waves into the passage, the ultrasound waves having sufficient power to exert a coagulating effect on the constituents, the coagulated constituents being pushed into a slag on the liquid metal as said liquid metal flows through said passage.

In another aspect of the present invention, there is provided a device for separating a liquid metal from a heterogeneous mixture of extraneous particles therein, comprising:

a passage for receiving a flow of liquid metal containing a heterogeneous mixture of extraneous particles; and a source for ultrasound waves arranged relative to the passage to direct the ultrasound waves therein and having sufficient power to exert a coagulating effect on the particles to change the progress of the particles through the passage.

In yet another aspect of the present invention, there is provided an ultrasonic detection device comprising an ultrasonic transmitting delay line and an ultrasonic receiving delay line, ultrasonic reflection means placed beyond the transmitting delay line and aligned therewith, the reflection means being dimensioned so that when immersed in a liquid and receiving ultrasonic waves from said transmitting delay line, the reflection means focuses the ultrasonic waves to a focal volume, said receiving delay line receiving reflected ultrasonic waves from extraneous particles in the focal volume allowing for their detection by said receiving delay line.

In still yet another aspect of the present invention, there is provided a delay line for use in an ultrasonic detection device used for the detection of particles in a sample of molten metal, said delay line comprising a body, a portion of said body being immersed in said sample and being formed of a single phase material, said material being an alloy, at least one constituent of which is common with said sample, thereby to minimize allotriomorphic changes which inhibit sound transmission through said delay line.

In still yet another aspect of the present invention, there is provided a method of degassing a liquid metal melt comprising the steps of:

i) providing a liquid metal melt and a source for ultrasound waves adjacent said melt;

ii) directing ultrasound waves into said melt to form a wave pattern in said melt; and iii) providing said ultrasound waves with sufficient power to cause cavitation to occur at antinodes in said wave pattern, said cavitation forming bubbles leading to degassing of said melt.

In still yet another aspect of the present invention, there is provided a device for detecting the surface level of a liquid melt, said device comprising an ultrasonic transmitting delay line and an ultrasonic receiving delay line, a first ultrasonic reflector placed beyond said transmitting delay line and aligned therewith, a second ultrasonic reflector placed beyond said first ultrasonic reflector and aligned therewith, said first and second reflectors being arranged so that when immersed in a liquid and receiving ultrasonic waves from said transmitting delay line, said first and second reflectors reflect said ultrasonic waves from said transmitting delay line to the surface of said melt, said first and second reflectors being further arranged to receive said ultrasonic waves reflecting from said surface and to reflect said ultrasonic waves toward said receiving delay line, wherein said ultrasonic waves reflected from said surface may be used in the determination of the level of said melt.

BRIEF DESCRIPTION OF THE DRAWINGS

Preferred embodiments of the present invention will now be described, more fully with reference to the appended drawings in which:

FIG. 1a is schematic view of a casting installation utilizing the present method;

FIG. 1b is a schematic sectional view of one portion of the installation illustrated in FIG. 1;

FIG. 3e is a graph relating particle count to threshold level for a number of water test samples;

FIG. 4a is a schematic view of another ultrasonic detection device;

FIG. 4b is a view taken on arrow 'X' of FIG. 4a;

FIG. 4c is a schematic view of another aspect of the device illustrated in FIG. 4a;

FIG. 4d is a view representative of a CRT display relating to the device illustrated in FIG. 4a;

FIG. 10b is a sectional view taken on line X—X of FIG. 10a;

DESCRIPTION OF THE PREFERRED EMBODIMENTS

Figure 1C:
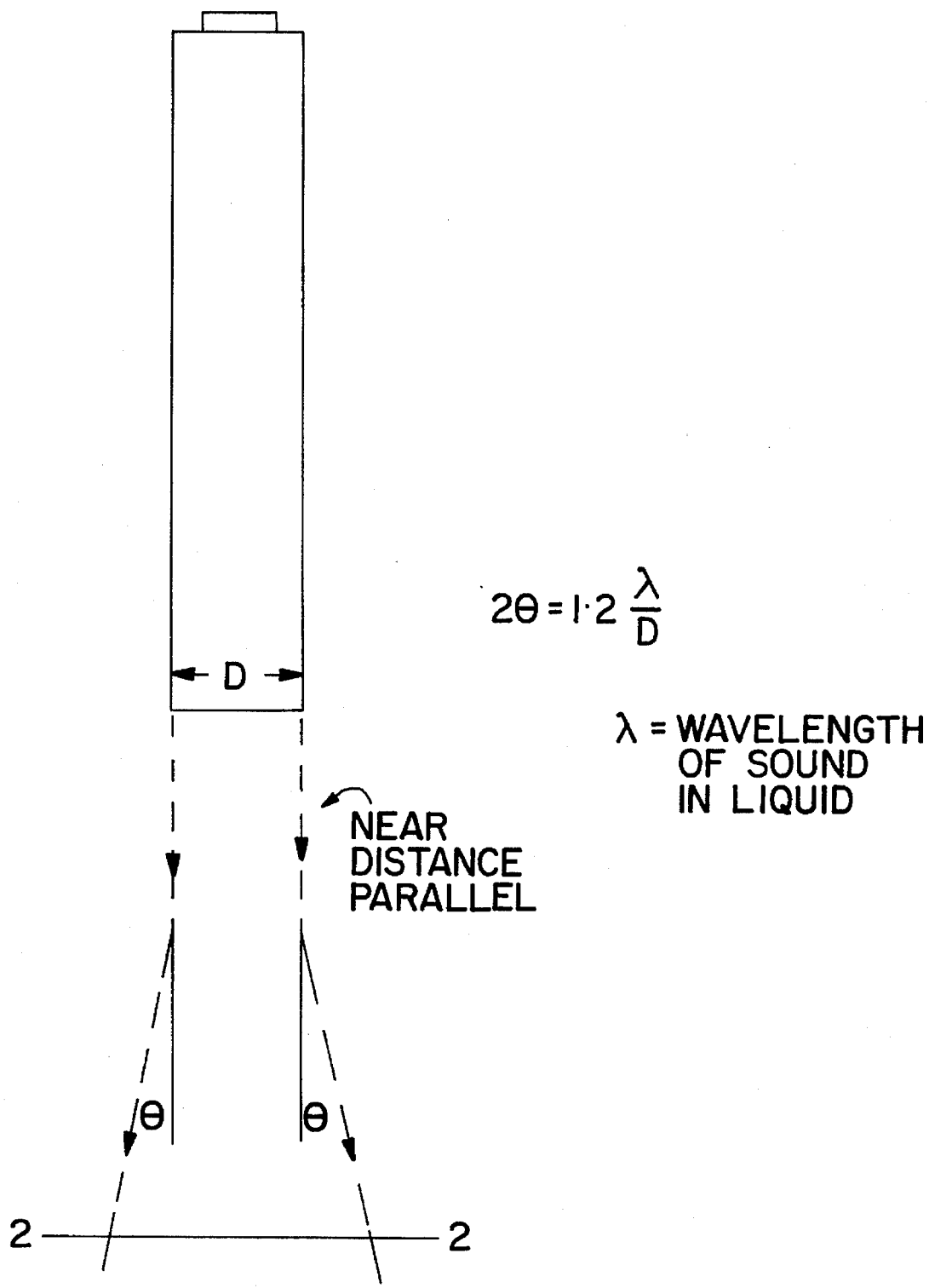
FIG. 1c is a schematic view of an ultrasound transmitting delay line.

As will be described herein below, a method which makes use of the principle of an acoustic filter, relying on the property of sound waves to exert a pressure within a liquid which can be used to coagulate contaminating particles in a liquid metal stream is provided.

An earlier suggestion for purifying liquid metal melts had been to use the properties of standing sound waves in order to force particles together, causing them to coagulate into larger particles which would in turn rise more quickly into the covering slag. Although this could be demonstrated, the process could not be made to deal adequately with all the liquid material.

According to the present invention, a situation is created in which the contaminated liquid flows through a passage from one container to another and at the same time a standing sound wave exerts a pressure on this flow causing contaminating particles to coagulate. The effect will be that the coagulated foreign particles will be acted upon by exerted pressure and pushed up into the slag on the surface of the liquid metal as the liquid metal flows through the passage.

The relative pressures exerted upon the particles is a function of two factors:

i) the acoustic impedance of the particles and the difference between these values and the acoustic impedance of the liquid medium; and ii) the magnitude of the sound waves must be sufficient to cause the particles to coagulate and must be reflected so that some of the sound waves act upon the coagulated particles to push them into the slag on the surface of the liquid metal as the liquid metal flows from one container to the next container.

In order to achieve the above, the shape of the passage is important, as are the materials used in forming the passage and the manner in which the sound waves are carded from the transducer to the liquid medium.

FIG. 1 shows a simplified diagram of a casting installation. A tundish is provided with a clean container 1 and a dirty container 2 separated by a housing 3. Of course, the clean and dirty containers could be formed from a singular container but with a wall replacing the housing 3. A ladle 4 is located above the tundish and has a transfer tube 5 through which liquid metal is delivered to the dirty container 2. The liquid metal typically contains extraneous particles in the form of oxides which may be picked up while in the ladle, or by reaction with entrained air in the hardware associated with the tube 5 or in the dirty container 2.

The housing 3 is provided with a passage 6 through which molten metal flows from the dirty container 2 to the clean container 1. Located below the clean container is a casting mold 7.

The housing 3 is further provided with a passageway 3a to receive an acoustic device 8. The acoustic device has a steel body (referred to herein below as the delay line) turned at the lower end to fit the vertical hole 3b in the passageway 3a and which narrows down, either in the form of a simple inverted conical form or in the form of an exponentially derived form to the smaller diameter.

The function of such a shaped delay line (that is the connecting medium between the hot liquid metal and the cooled piezo transducer of the acoustic device 8) is two fold:

i) to enable a large and powerful piezo transducer shown at 9 to be applied at the top of the large diameter portion of the acoustic device 8; and ii) to provide a heat sink for the smaller immersed end of the delay line.

This design assists in the cooling required to control the dissolution of the remote end of the delay line 8a and to limit the amount of gamma iron (as disclosed in U.S. Pat. No. 4,981,041) which inhibits sound transmission through the remote end 3a of the delay line.

At the top of the delay line is fixed the piezo transducer 9. Cooling coils 10 are embedded in a heat shield 10a whose purpose is both to cool the transducer 9 and to keep the liquid-metal interface between the remote end of the delay line 8a and the liquid metal 11 thermally stable. The passageway 3a extends beyond the passage 6 and receives therein a plug of refractory material 12. The plug 12 has an inner slightly inclined face which borders the passageway and is aligned with the remote end of the delay line. The inclined face forms a reflector 12a in the passage 6 opposite the remote end of the delay line which is arranged to reflect sound waves back to the delay line to create a standing wave in the passage as well as to reflect some sound waves upwardly into the passage towards the clean container. This plug 12 is of an erosion resisting form of refractory, for example a derivative of $ZrO_2$, $Al_2O_3$ or other suitable materials.

In use, metal flows from the ladle 4 via the transfer tube 5 into the dirty container 2. From here it flows through the passage 6, past the reflector 12a and the delay line 8a and into the clean container 1 from whence it flows down into the casting mold 7. As the metal flows through the passage, the powerful sound waves which form the standing wave in the passage, cause particles 13a entrained in the metal to coagulate at the nodes of the standing wave. The flow of the metal through the passage also causes coagulated particles at the nodes to flow through the passage towards the clean container 1. The sound waves that are reflected by reflector 12a upwardly into the passage push the coagulated particles up into the slag on the upper surface of the liquid metal allowing for their removal.

Whereas the temperatures in the tundish may be held at 1560° C. to 1585° C. and the melting point for low carbon steel is 1520° C. there may be problems in actually wetting the remote end of the delay line 8a by dissolution. This can be overcome by aluminising the immersed end of the delay line 8a, or by using the appropriate grade of steel for its manufacture, i.e. of higher carbon content than that of the liquid steel.

The wetting problems may be minimized by forming a conical remote end on the delay line 8a which may be imposed into the passage 6 which will be melted away by the passing liquid steel, with the liquid steel-delay line interface ending up as shown by the solid line in FIG. 1b.

It has been discovered through the present method that the sound waves travelling along such delay lines do so in the form of beat pulses. The pulses emanate from the end of the delay line at frequencies proportional to the inverse of the radius of the smaller or smallest diameter but within the pulses, the frequencies will be of the same order as the driving piezo transducer 9.

The latter must be designed for high power and of the order of several hundred watts. The silvered surfaces should be approximately the same diameter as that of the larger diameter of the delay line 8a and the transducer 9 should be some millimeters larger still. This will provide the longest possible gap across which a spark can occur.

The silvered surfaces spread the effect of the high voltage current uniformly across the transducer volume, thus contributing to the uniform extension and compression of the transducer in its piezo effect. The higher the voltage between these plates or silvered areas, the more powerful the piezo effect. If the voltages applied are too high, then there will be sparking around the transducer and damage will occur. If the transducer is in air, then the dielectric coefficient for air will be the limiting factor as well as the total air path for voltage breakdown. For example, a transducer operating at 500 kilocycles per minute should be approximately 2.5 millimeters thick. If the silvering is limited to within 2.5 millimeters of the edge of the transducer then the air path for sparking will be:

$$3 \times 2.5 \text{ mm} = 7.5 \text{ mm}$$

For air, it is accepted that one needs approximately 30,000 volts for a spark to cross 25 mm of air. Therefore, the limiting voltage will be:

$$(7.5 \text{ mm})/(25 \text{ mm}) \times 30,000 \text{ volts} = 9000 \text{ volts}$$

By using encasing techniques with materials having higher dielectric properties, a better value could be obtained. The voltage used on measuring instruments is much lower, namely between 350 volts and 900 volts. Normally, these transducers are silvered to the edges. If this were done in the case of the power transducer array, the limiting voltage would be 3000 volts. Back to back transducers could also be used, provided this effect is taken into account.

It will be understood that other passage configurations may also be appropriate. However, one should bear in mind that any increase in the constriction of the passage may be a detrimental effect on the overall efficiency of the device. The immersion of any transducer in such a passage, for example, may make the choice of material acting as the transmitter difficult, in view of extreme sound losses that may arise from poor acoustic matching.

It may be appropriate to provide a gate upstream of the stepped passage to prevent initial irregular flow which might prevent the complete and immediate wetting of the delay line.

The smaller diameter of the delay line may be lengthened in order to provide additional cooling at the bottom and to allow the delay line to be used several times.

Another aspect of the present invention relates to the detection of extraneous particles in a liquid using sound and in particular, ultrasound. High frequency sound pulses passed into liquid are reflected by extraneous particles suspended in liquid if they exhibit different acoustic properties than those of the liquid. Thus, ultrasound can be used to detect extraneous particles in a liquid; however, the fundamental characteristics of the sound pulses need to be taken into account. For example, a sound beam spreads out as the sound beam moves away from the source as is shown in FIG. 1c. This property can be calculated and compensated for in the design of an ultrasound particle detection device. Specifically, high frequency sound waves can be used to detect extraneous particles suspended in liquids, by:

i) passing a sound beam though the liquid and; thereafter ii) measuring the scatter or attenuation caused by the fact that the particles deflect the sound waves in small increments and thus, diminish the total power of the sound beam as it progresses through the liquid.

In this case, the power of the sound diminishes as a function of:

a) the concentration of the particles;

b) the distance that the sound waves have to travel through the mixture; and c) the frequency of the sound waves.

This sound loss can be measured and then, knowing the distance of travel, a value for the concentration of particles determined.

In the case of aluminum alloys, it is known that clean material can readily be distinguished in the broad sense from that contaminated by oxide films, but the exact nature of the contamination is difficult to measure in this way. A large number of small particles could produce the same effect as a relative few particles of an intermediate size whilst a few extremely large and possibly dangerous particles may not be detected.

With this aspect of the present invention, one has the ability to discriminate and quantify each of the various categories in order to obtain a quantitative assessment of the liquid metal quality. Furthermore, by using a delay line in rod form, the sound waves emanating from the delay line into a liquid will be transmitted though the liquid in the form of a substantially parallel beam over relatively short distances (that is up to 20 centimeters). That is to say, the sound beam on leaving the circular end of such a delay line widens only slightly as it travels through the liquid.

Figure 2:
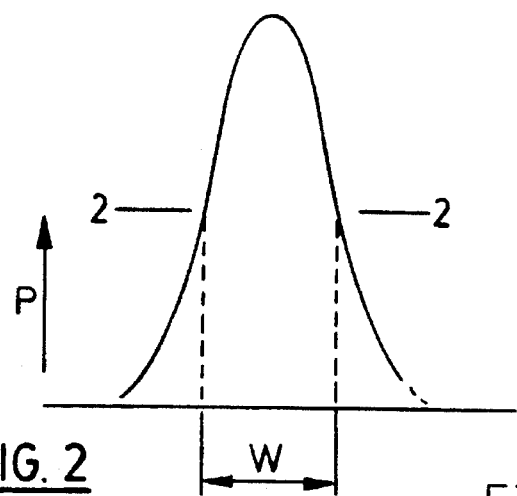
FIG. 2 is a graph relating beam width and power.

The definition of beam width is the distance of the outer boundaries of the beam on the cross-section of the beam where the power has been reduced by 50%. FIG. 2 shows the typical cross-section relating beam width and power, with line 2—2 illustrating the 50 percent level.

Figure 3A:
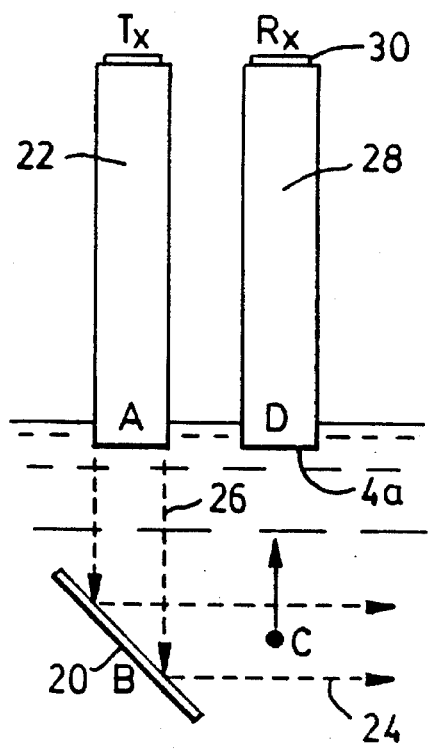
FIGS. 3a and 3b are schematic views of an ultrasonic detection device.
Figure 3B:
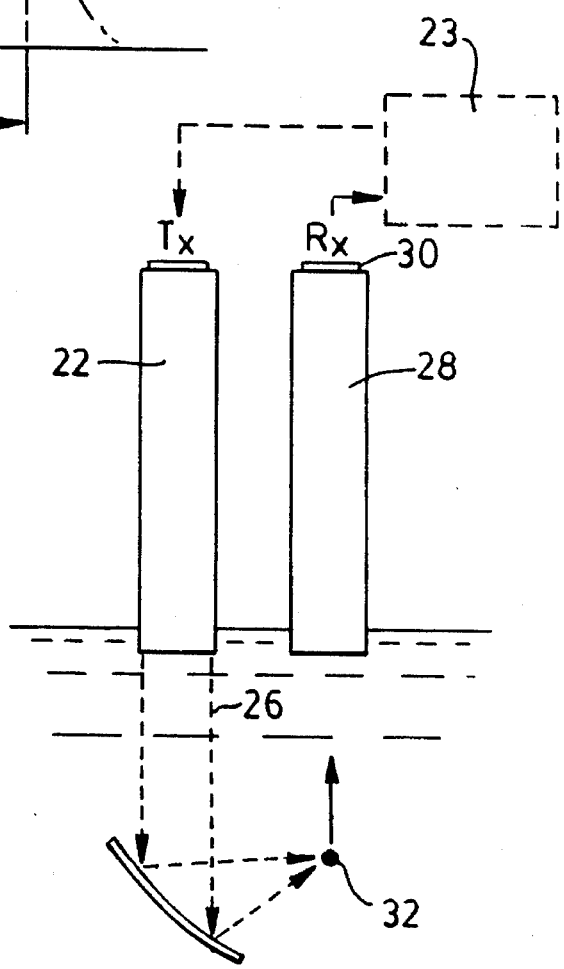

Referring to FIGS. 3a and 3b, if such a beam of sound pulses impinges upon a reflector, shown at 20, the beam will be reflected in relationship to the angle of the beam with respect to the reflector in a similar manner to light.

Figure 3C:
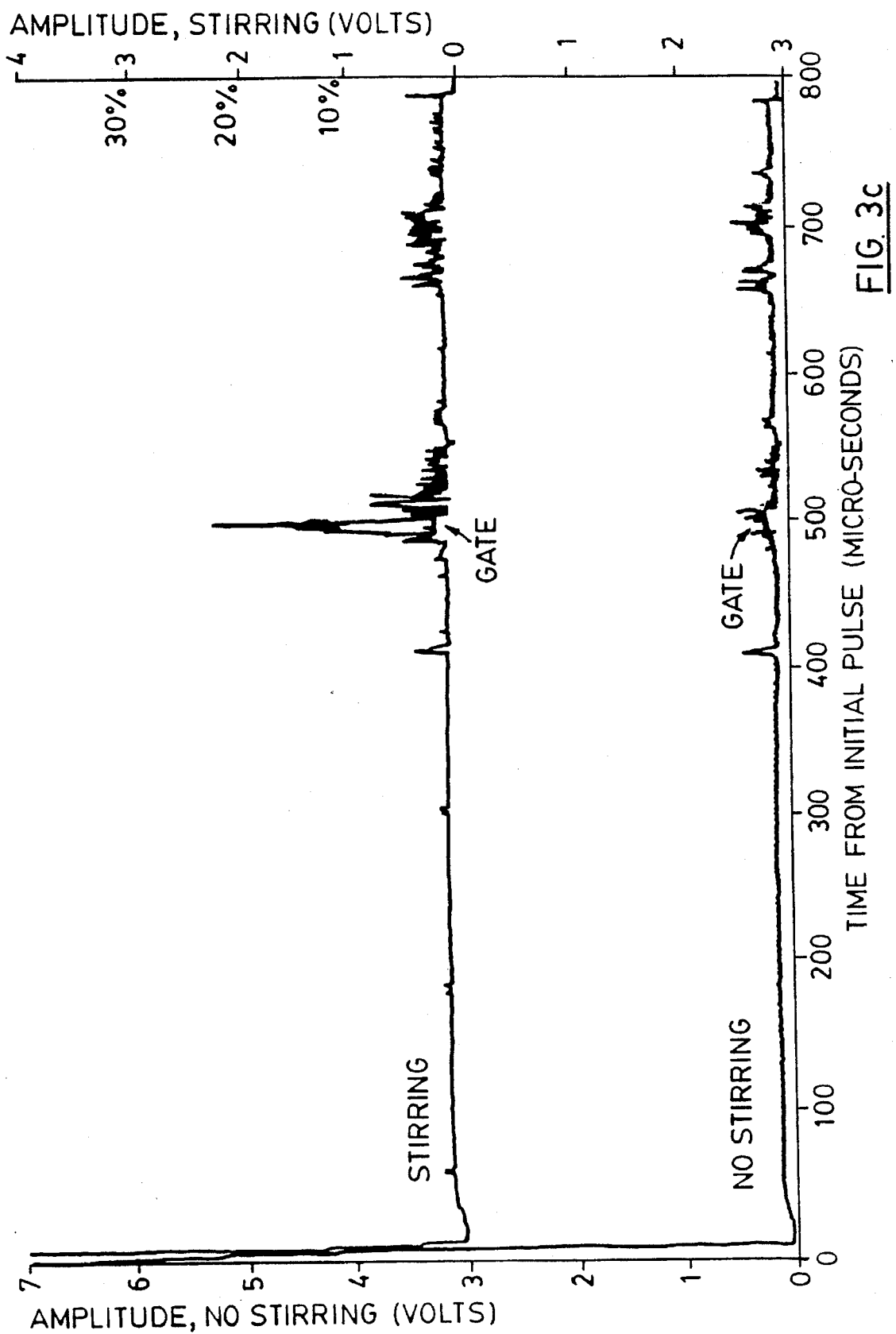
FIG. 3c illustrates the relationship between a pulse and a time base.
Figure 3D:
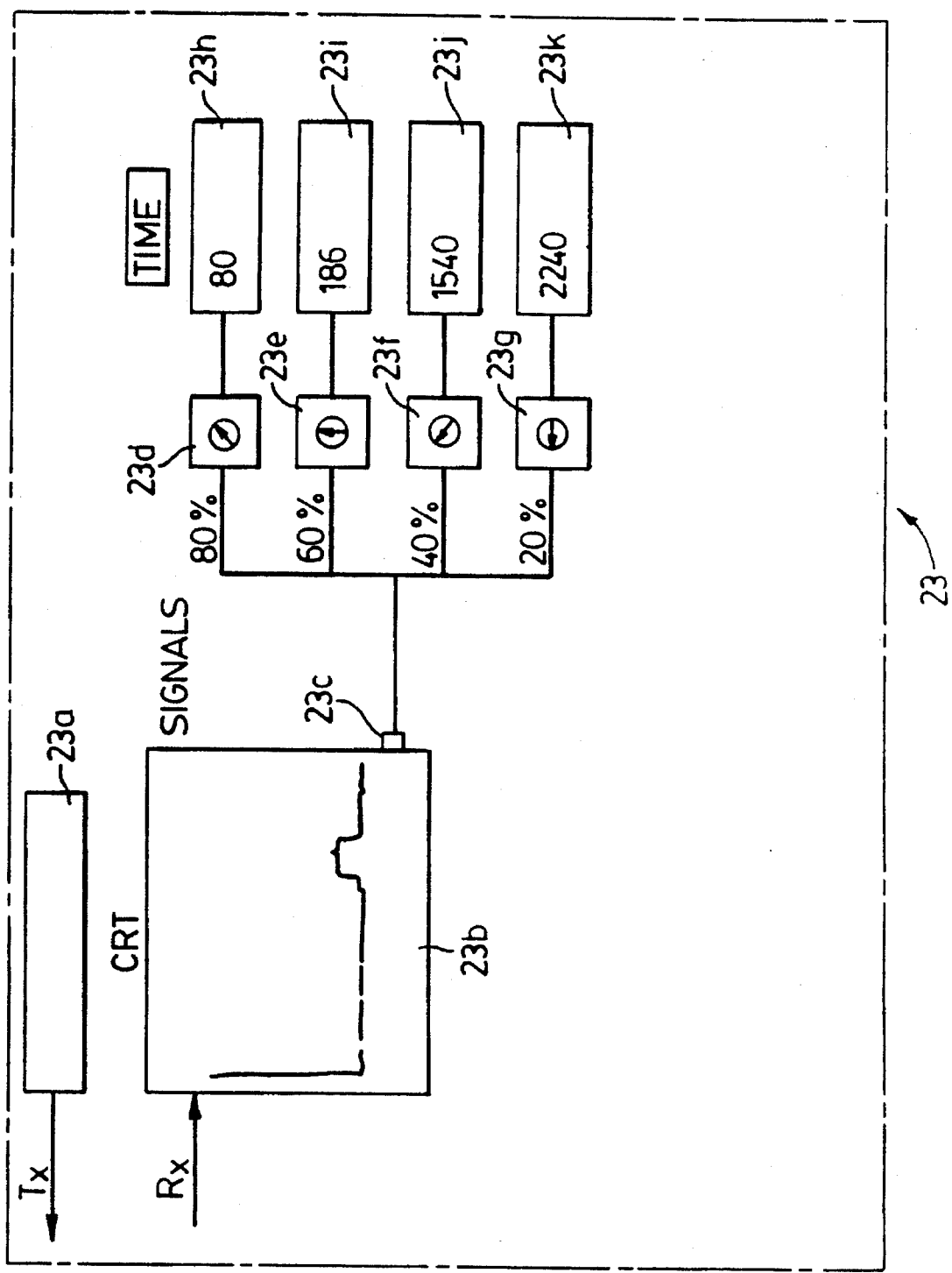
FIG. 3d is a schematic view of a portion of the device illustrated in FIG. 3b.

The transmitting delay line 22 and the receiving delay line 28 each communicate with a central controller shown at 23, the latter of which is better illustrated in FIG. 3d. The controller 23 includes a sound pulse generator 23a which communicates with the transducer ahead of the transmitting delay line 22. A CRT 23b displays the signal being received from the receiving transducer 30. A gate outlet 23c is provided on the CRT 23b and communicates with a number of gate circuits 23d to 23g. Each gate circuit conveys signals relating to particle count to an associated counter 23h to 23k respectively.

If the delay line 22 is in the vertical position and a reflector 20 is set at an angle of 45 degrees in the liquid medium, then the reflected sound beam shown at 24 will be turned at right angles to the incident delay line axis. The width of the reflected beam will be substantially the same as that of the incident beam.

The reflected beam can be made to pass directly under a second vertical delay line, shown at 28, having a receiving transducer 30 at one end. Should there be particles directly under this receiving delay line 28 then relatively small pulses will be reflected from the particle and a small signal will pass upwards across the interface of the liquid and remote end of the delay line (as shown at 28a), up the delay line and be recorded by the receiver transducer 30. This technique allows for improved discrimination of size and concentration of such particles.

Referring to FIG. 3b, the reflector 20 has a concave shape 20a so that the sound beam can be focused into a small area (referred to as the focal volume 32). This increases the power at the focal volume 32.

Under normal conditions, pulses received from the liquid can be selected as they appear over very short time spans. This is illustrated in FIG. 3c showing the use of an electronic 'gate' on the time base of the controller 23 shown in FIG. 3d. By selecting this 'gate' to cover the position of the focal volume of the sound beam, the number and size of particles entering the focal volume can be measured and counted. This is especially suited to the detection of large and potentially damaging particles which, one can assume, will have an increasing probability of passing through the focal volume with an increased time period during which incoming signals are counted. It follows then that it is desirable to optimize the shape of the focal volume in order to maximize the probability of detecting these large particles. Thus, a better sample can be obtained by carrying this counting procedure over a period of time.

Furthermore, the 'gate' may be associated with what is termed a threshold circuit. This can be set so that each time a pulse is initiated and reflection detected, the level at which this is recorded can be prearranged, i.e. a large signal (corresponding to a large particle) will register while a smaller signal (corresponding to a smaller particle) will not register. FIG. 3c indicates several threshold levels, wherein the illustrated signal is breaking through the 20 percent level but does not reach the 30 percent level. Therefore, the signal would be counted at the 20 percent level and not at the 30 percent level.

Together, the devices illustrated in FIGS. 3b and 3d operate on two variables:

i) the length of the time base which determines the number of pulses per microsecond that can be employed; and ii) the length of time necessary for the pulse to travel the whole of the required distance and return to be registered.

With a long time base, that is that required for the examination of a steel slab some 50 inches wide, the total time of travel of the sound will be in the order of:

$$50 \times 25.4 \times 2/5.9 = 430 \text{ microseconds, where:}$$

50 is the length in inches;

25.4 is conversion to millimeters;

2 is for the double path; and 5.9 speed of sound in steel in millimeters per microsecond.

If these pulses are sent one after the other then there could be as many as 1,000,000/430=2325 pulses per second. This would likely cause echoes from one pulse to be recorded on a previous pulse time base. Hence the repetition rate may be slowed down to allow this echo activity to die away completely between pulses. In the present case, the repetition rate is held at 270 pulses per second.

If the threshold level is held very high, then only the very large particles will break this level. For example, if counting is carried out over a specific time period, say 10 seconds, then there will be 2,700 distinct pulses. During this time, there might only be say 20 counts registered, namely those from particles that are sufficiently large to generate a signal beyond the threshold. The frequency of these can be related to the base 2,700 pulses as a percentage of those. Therefore, the percentage count frequency for these large particles would be:

$$(20)/(2700) \times 100 = 0.7\%$$

If, on the other hand, the threshold level is set at a lower level at which some 1,600 counts. are registered for the 10 seconds, then the count would be:

$$(1600)/(2700) \times 100 = 59.2\%$$

Thus, signals recorded from the liquid metal are recorded faster than the eye can see and by having a number of these threshold circuits, namely:

i) with different threshold values and thus different particle sizes;

ii) each with its own counter; and iii) all deriving their information from the gate.

The collective information from these threshold circuits can be related to the size distribution of the particles in the liquid metal.

It should be noted, however, that:

i) with the threshold set for the larger particles, this first measure will be of those and perhaps the even larger ones;

ii) when setting the lower thresholds the larger ones are also being counted; and iii) one may require a larger time period to count the less frequent large particles.

FIG. 3e illustrates the results of a water model test wherein two different mixtures of particles were examined under three different degrees of agitation to simulate different degrees of particle content in the liquid. The results are shown in terms of threshold count, plotted as a percentage over a time period. The resultant curve (in dashed lines) gives a measure closely related to the contamination of the liquid by the particles.

Computer techniques can of course simplify these procedures. In addition, although four threshold circuits are shown, any number may be used depending on the number of particle size groupings desired.

It should be borne in mind that this particle detection technique provides answers as to size of particles, but not as to what their form might be. Are they crystalline or jagged or spherical, or are they in the form of clusters or continuous film? The embodiment illustrated in FIGS. 4a, 4b and 4c is provided to answer these questions.

Given the same set up with transmitter and receiver delay lines and again using a reflector 36, the latter can be shaped like an open book instead of rounded and concave. The effect on the sound beam will be to focus the beam into a focal volume in the form of an elongated cylinder.

The conventional deflection modulations of the signal would give a number of signals, but if they are recorded by intensity modulations on a suppressed time base, they would come up as a series of points of light, the intensity of which would be relative to their size on the time base line CF2F1.

By pivoting the whole apparatus on the axis C—C, the axis of the delay line D—D would be swept over an arc of liquid. The signals to be recorded would be received on a conical shape within the liquid. Particles of spherical form would show as repeated points of light whereas those of rotating irregular shapes would appear to scintillate. Larger clusters may show a relatively wide area of signal intensity whilst films of oxide may appear as a string.

An illustration of this data is shown in FIG. 4d. Liquids studied in this way should provide similar information to that obtained on radar screens as to size and characterization of returns.

Figure 4E:
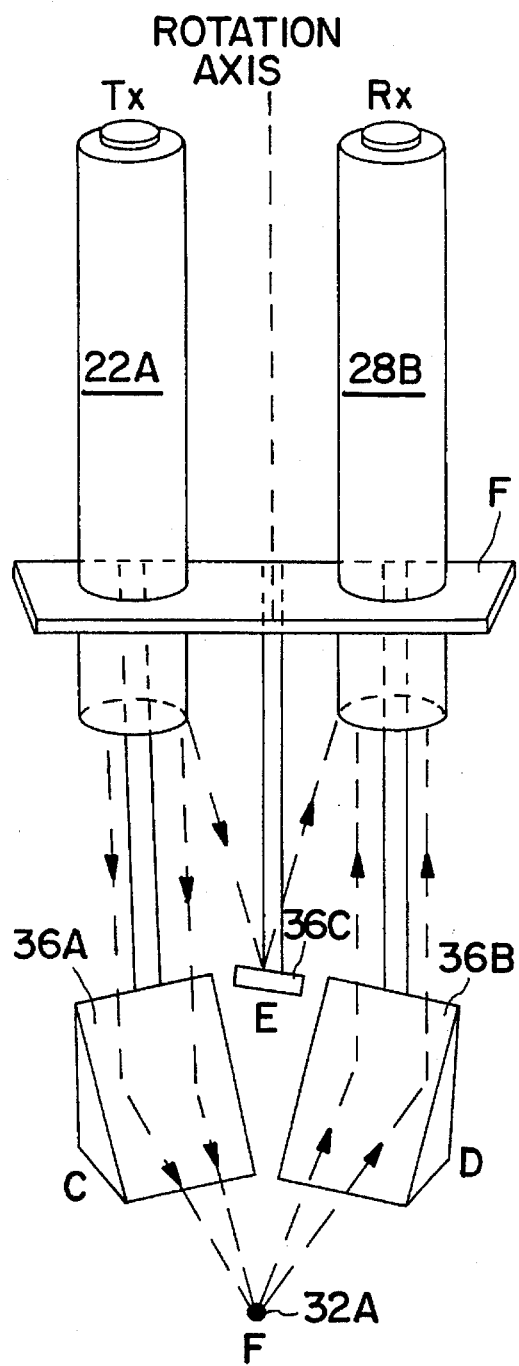
FIG. 4e is a schematic view of another embodiment of an ultrasound detection device.
Figure 4F:
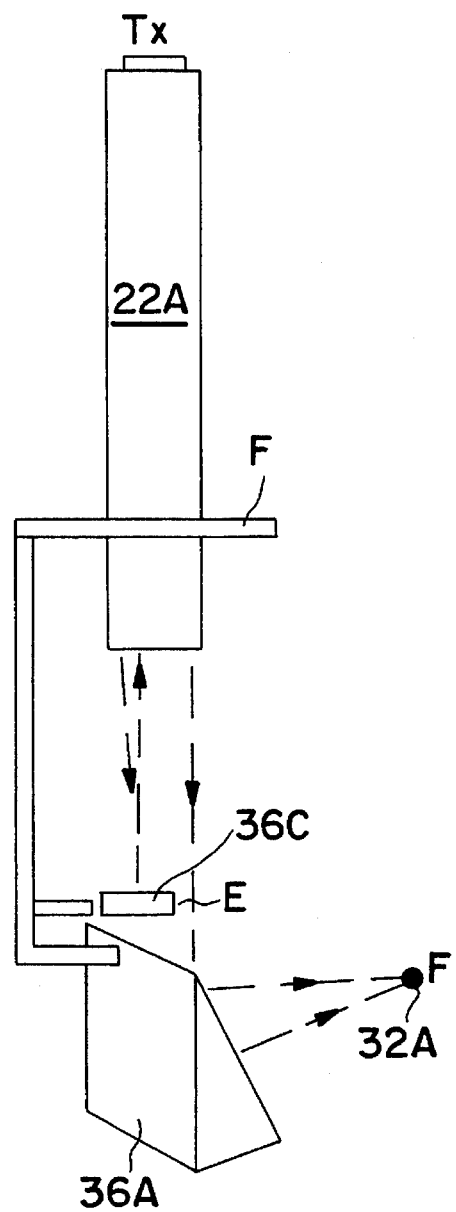
FIG. 4f is a side view of the device illustrated in FIG. 4e.

FIGS. 4e and 4f show yet another embodiment of an ultrasound detection device similar to that shown in FIG. 4a. Moreover, in this embodiment, two reflectors 36A and 36B are used, one 36A of which is positioned below the transmitting delay line 22A and the other 36B of which is positioned below the receiving delay line 28B. Ultrasound generated by the transmitting delay line 22A is reflected by the reflector 36A to a focal volume 32A. Reflected ultrasound from the focal volume 32A is directed to the receiving delay line 28B by reflector 36B. The two reflectors 36A and 36B, the transmitting delay line 22A and the receiving delay line 36A are mounted on a frame F which is pivotable about a central axis of rotation AOR to allow the focal volume 32A to be swept over an arc of the liquid. In addition to reflectors 36A and 36B, a reflector 36C is positioned between the two reflectors on the axis of rotation AOR. Reflector 36C is also mounted on the frame F and pivots with the other components when the frame is pivoted. The third reflector makes use of the fact that the ultrasound generated by the transmitting delay line 22A spreads out as it moves away from the transmitting delay line. The reflector 36C reflects ultrasound directly back to the receiving delay line 28B. The ultrasound reflected by reflector 36C and received by the receiving delay line 28B is used to measure the attenuation of the liquid. The frame F can also be moved vertically so that the ultrasound can be swept over a true volume of the liquid.

With such three-dimensional recording, it will be possible to identify better particle shapes. Spherical slag particles will register steady signals while angular particles rotating about their own axes will register scintillating signals. Films will show up as light areas. Thus, with three-dimensional recording, holographic methods of recording will be better suited than recording with a cathode ray tube.

Ultrasonics at various frequencies can be transmitted into liquid metals by way of delay lines, preferably of the same material as that being examined or treated. This enables the heat sensitive transducer to be removed from the hot zone of the solid-liquid interface while the good acoustic matching of the liquid metal and the material of the delay line reduces reflection losses to a minimum. The delay lines may be of rod-like shape and can either be introduced vertically through the open top surfaces of the liquid metal or introduced through the sides of the vessel.

It is generally known that cooling needs to be applied, in the case of steel, close to the interface as indicated in U.S. Pat. No. 4,981,045. Notwithstanding this cooling, there remains the danger of the liquid steel breaking though the refractory lining of the vessel at the junction with the delay line and burning through the outer wall of the vessel.

As will be described, the embodiments shown in FIGS. 5 to 7 make such a junction safe and provide effective cooling along the length of the delay line.

Figure 5:
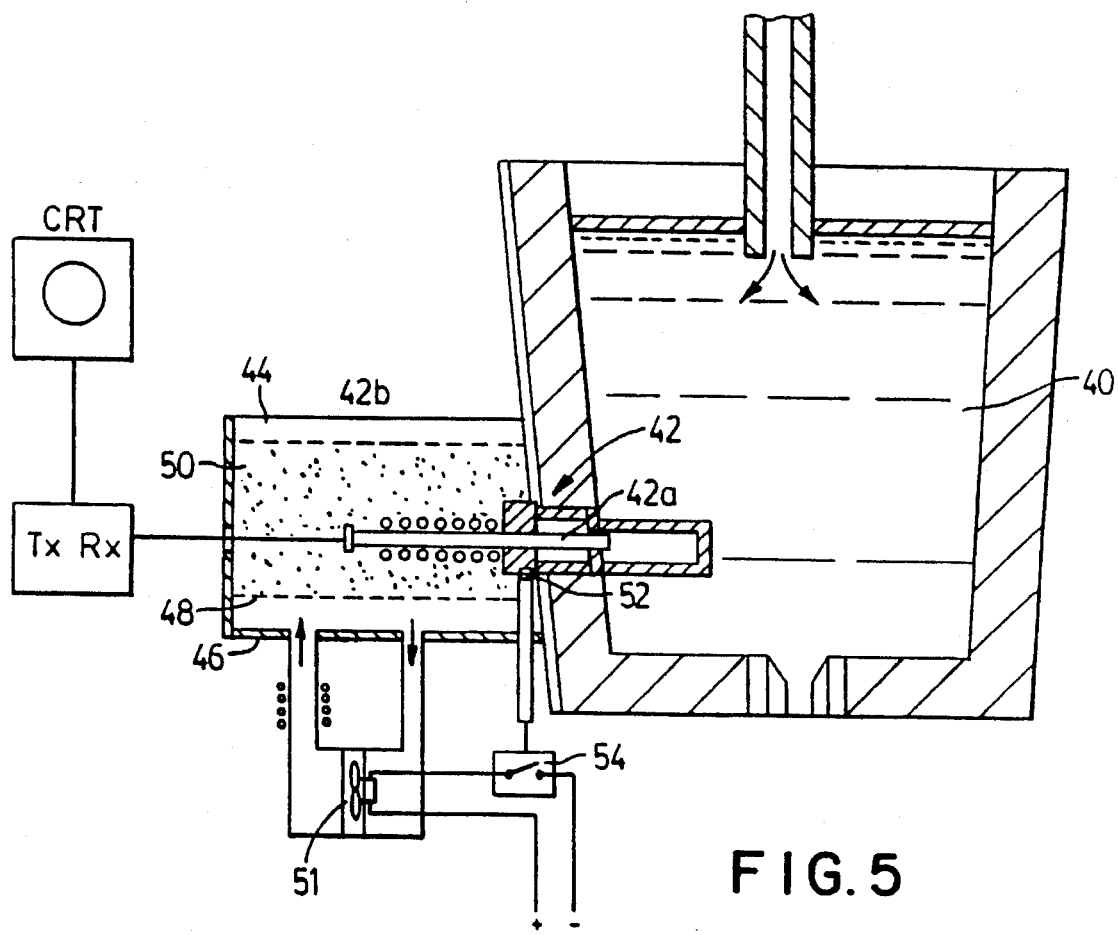
FIG. 5 is a schematic sectional view of another casting installation.

Referring to FIG. 5, a vessel is shown at 40 in the form of a steel tundish such as is used in the continuous steel casting process. Extending through one side of the vessel 40 is an ultrasonic measuring instrument 42 having a delay line 42a and which may be used to emit sound beams for examining or treating the liquid metal as well as an acoustic head 42b. Attached to the tundish is a steel box 44 which surrounds the delay line 42a. To the bottom of the box is welded a plate 46. Fixed to the inner face of the box a short distance above the plate 46 is a fine diaphragm 48 of mesh material capable of containing a granular refractory powder material 50, of sufficient quantity to cover the delay lines and their attached acoustic heads 42b completely. The total depth of this refractory material is such to provide sufficient blockage to any liquid steel penetrating or attempting to penetrate it.

Located between the plate 46 and the diaphragm 48 is a chamber having an inlet and an outlet formed in the plate 46 to receive a flow of air or inert gas from a blower 51. In this manner, the refractory powder material will become fluidised and if the gases are cooled it will provide an improved cooling system for the delay lines.

Located at the point of entry of the delay line 42a through the outer wall of the tundish is a thermocouple 52 which is coupled to a switching circuit 54. Circuit 54 in turn is coupled between a power supply and a blower 51. In this manner, any rise in temperature, such as would occur if liquid steel broke through the outer wall of the tundish may give rise to voltage changes from the thermocouple which in turn is used to switch off the fluidizing gases. The fluid bed would then collapses into a compact mass which inhibits any considerable flow of liquid metal.

Another approach is shown in FIGS. 6 to 9 in which the whole of the tundish, shown at 60, is extended to form a false pocket 62. In this case, should any breakout occur, the enclosed steel and refractory construction of the pocket 62 acts as a receptacle. Should metal flow into the interior space of the pocket 62, apart from the relaxation of the fluidised material into a solid barrier to flow, there would be the contained height equivalent to the liquid level in the rest of the tundish container.

A particular feature of this embodiment is that the ultrasonic delay line array can be located adjacent the exit of the tundish as shown at 64. This would be especially suitable for slab casting tundishes.

Figure 6:
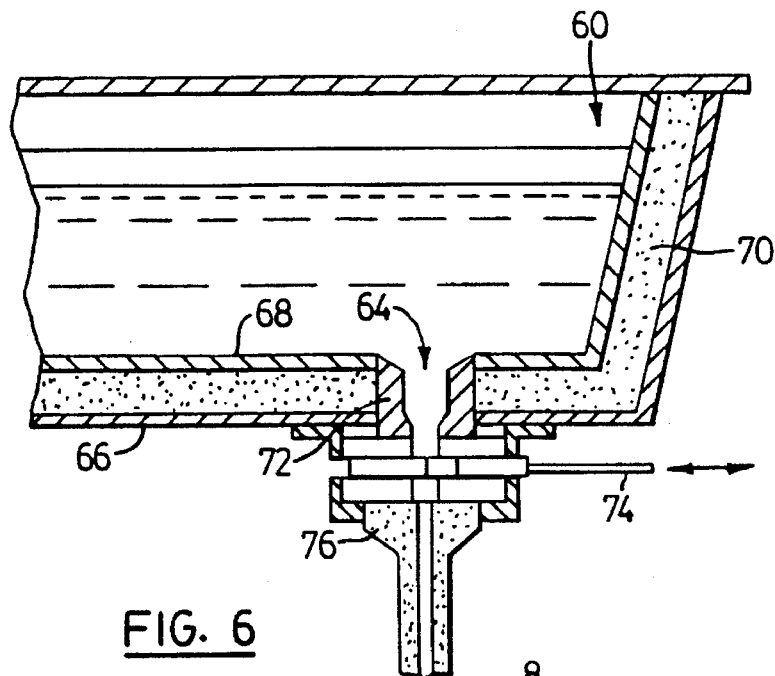
FIG. 6 is a schematic sectional view of yet another casting installation.
Figure 7:
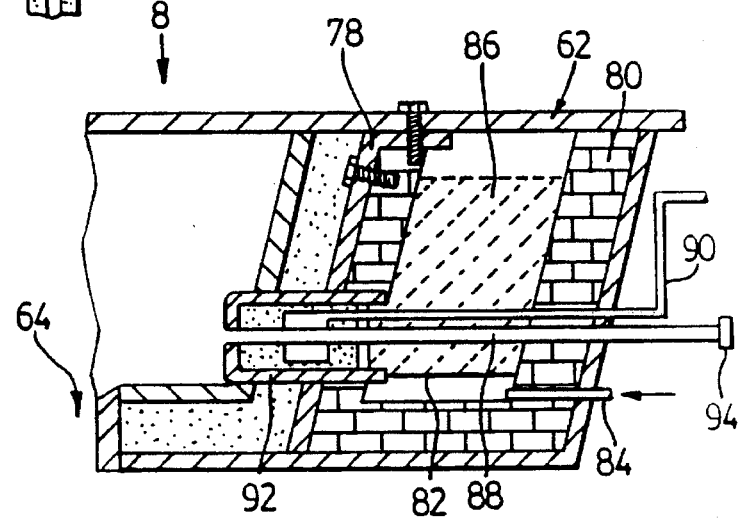
FIG. 7 is a schematic sectional view of a variation of the casting installation illustrated in FIG. 6.

As shown in FIGS. 6 and 7, the tundish 60 has a steel shell 66 and a lining board 68 with backing sand 70 located therebetween. An outlet nozzle 72 is located upstream of a slide gate control which in turn is upstream of a transfer nozzle to deliver molten steel to a mold. The pocket 62 has a steel end plate 78 bolted in place with a refractory brick lining 80. A porous screen 82 contains refractory material 86 located in the pocket 62. A passage 84 is provided in one wall of the pocket 62 for delivery of fluidizing gas into the pocket 62. An ultrasonic delay line is shown at 88 which is further provided with a passage for a gas or vapour cooling jacket formed within a graphite or alumina ceramic head 92. An ultrasonic transducer is provided at the cool end of the delay line as shown at 94.

One of the main advantages of such a system is that it allows a quality measurement to be made as the metal exits into the mold. This is the one area of measurement which could be consistent with measuring the overall quality and the point where the time system of marking defective areas in zones could be correlated with the sonic measurements. In other words, should a quantity of poor quality steel, that is with an undesirable level of inclusions, suddenly appear at the exit, action can be taken perhaps to label the slab formed therefrom as of lower quality or to remove the resulting slab from the line completely.

A further advantage is that the delay line can be changed to a transmitter of sufficient power to be switched on as soon as there is an indication of large clusters being present and blow them away from the orifice. Often there is evidence of 'vortexing' due to movement of the liquid metal in the tundish which drags down slag into the mold.

Figure 8:
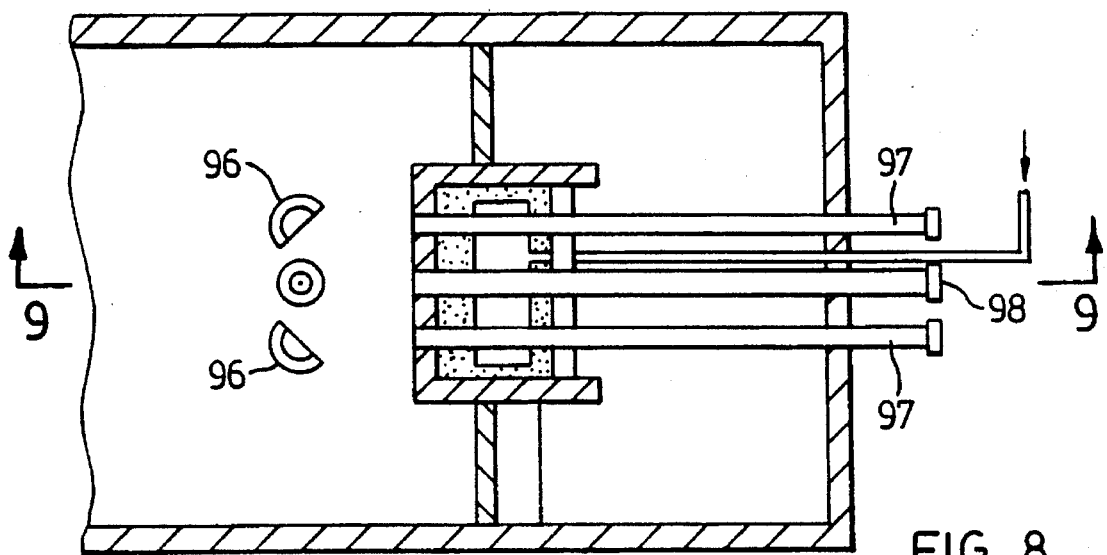
FIG. 8 is a schematic plan view of another variation of the casting installation illustrated in FIG. 6.
Figure 9:
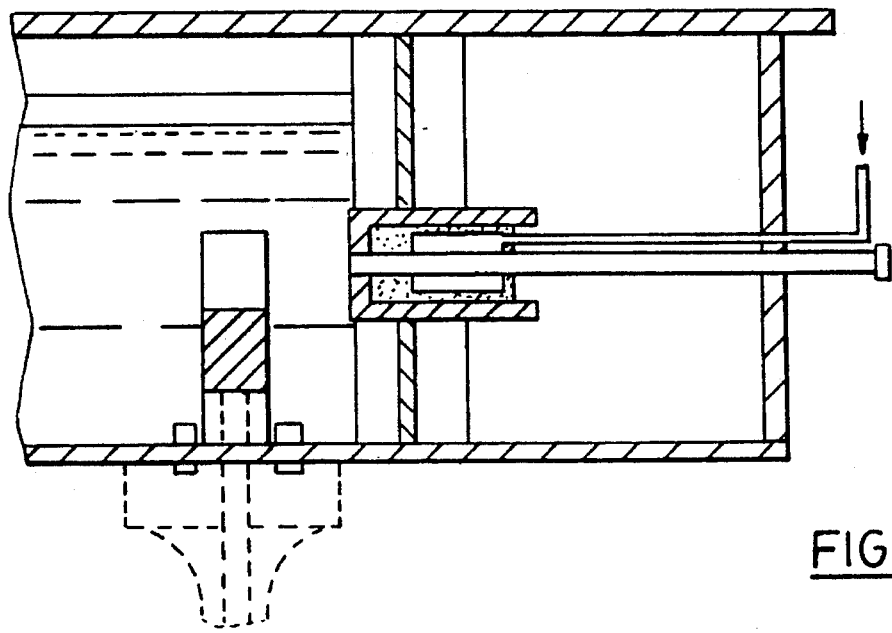
FIG. 9 is a schematic side elevation view taken on line 9—9 of FIG. 8.

An arrangement to achieve the above is indicated in FIGS. 8 and 9 and includes two transmitters 1 and 3. The central delay line acts as a receiver for detecting particle reflections and may be convened to a cleaning mode with the central rod acting as a powerful sound source pushing the particles aside from the outlet.

Suitable reflectors 96 are set on opposite sides of and aligned with the outlet orifice and in line with the corresponding transmitting delay lines 97. In this manner, the transmitting delay lines can be used in a number of modes as described above. For example, the two transmitting delay lines 97 can be used to provide alternative transmission lines with the central receiving delay line 98 used for both. From this would be derived a degree of redundancy as may be required in some instances where one transmitting delay line ceases to function.

Measuring the Liquid Level in the Tundish

Another problem is the maintenance of liquid levels in the tundish. If these levels fluctuate then the flow control devices used in the tundish to keep back slag and other extraneous inclusions do not function as effectively.

Figure 10B:
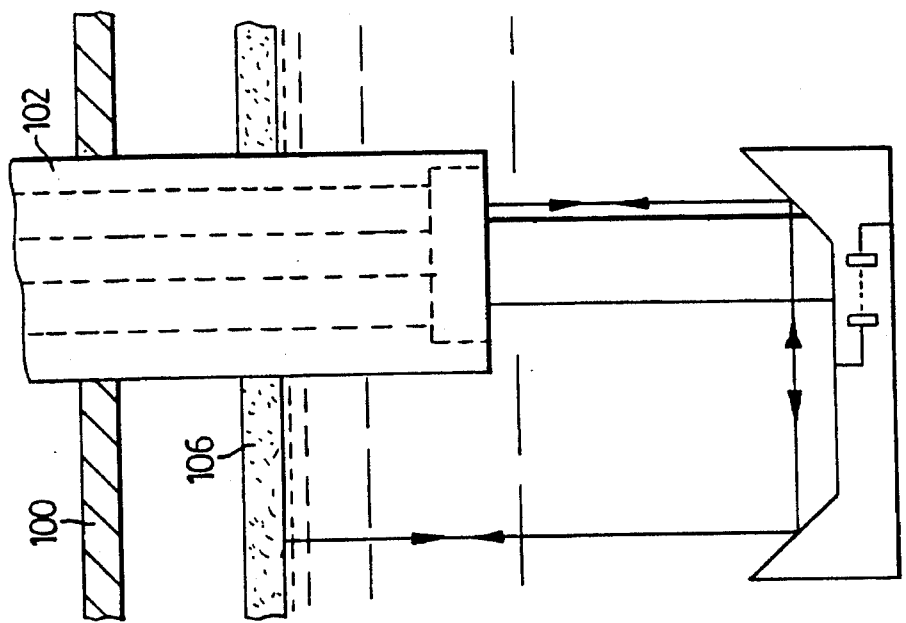
Figure 10A:
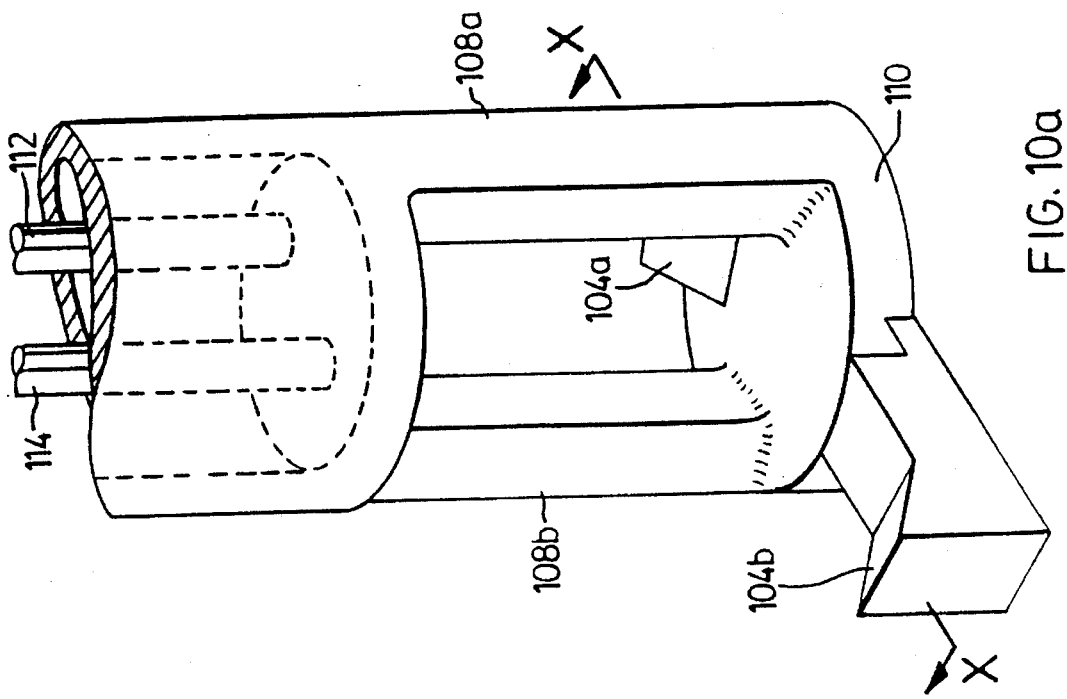
FIG. 10a is a fragmentary perspective view of another ultrasonic detection device.
Figure 11:
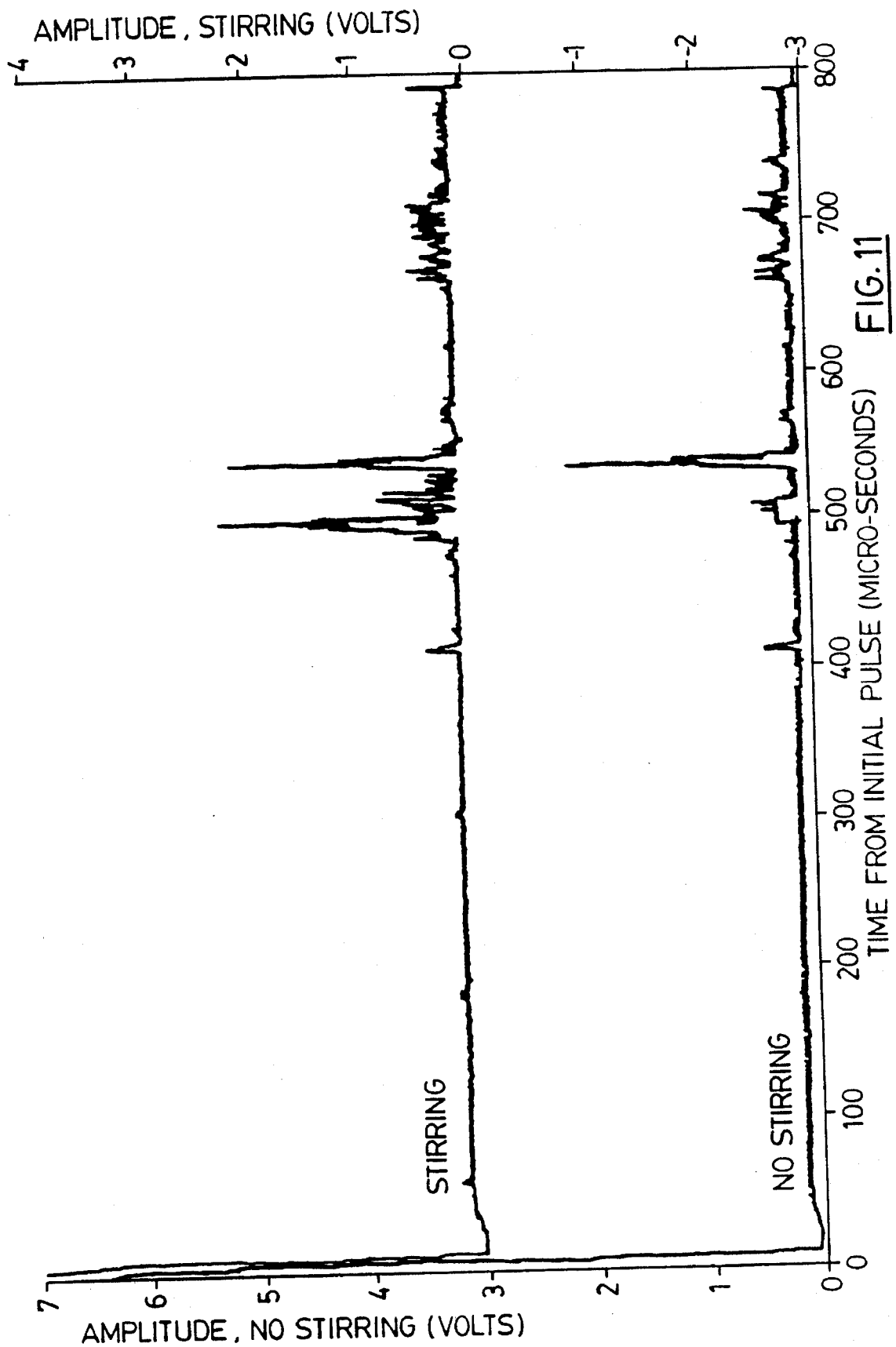
FIG. 11 is a graph relating amplitude to time for the device illustrated in FIGS. 10a and 10b.
Figure 12:
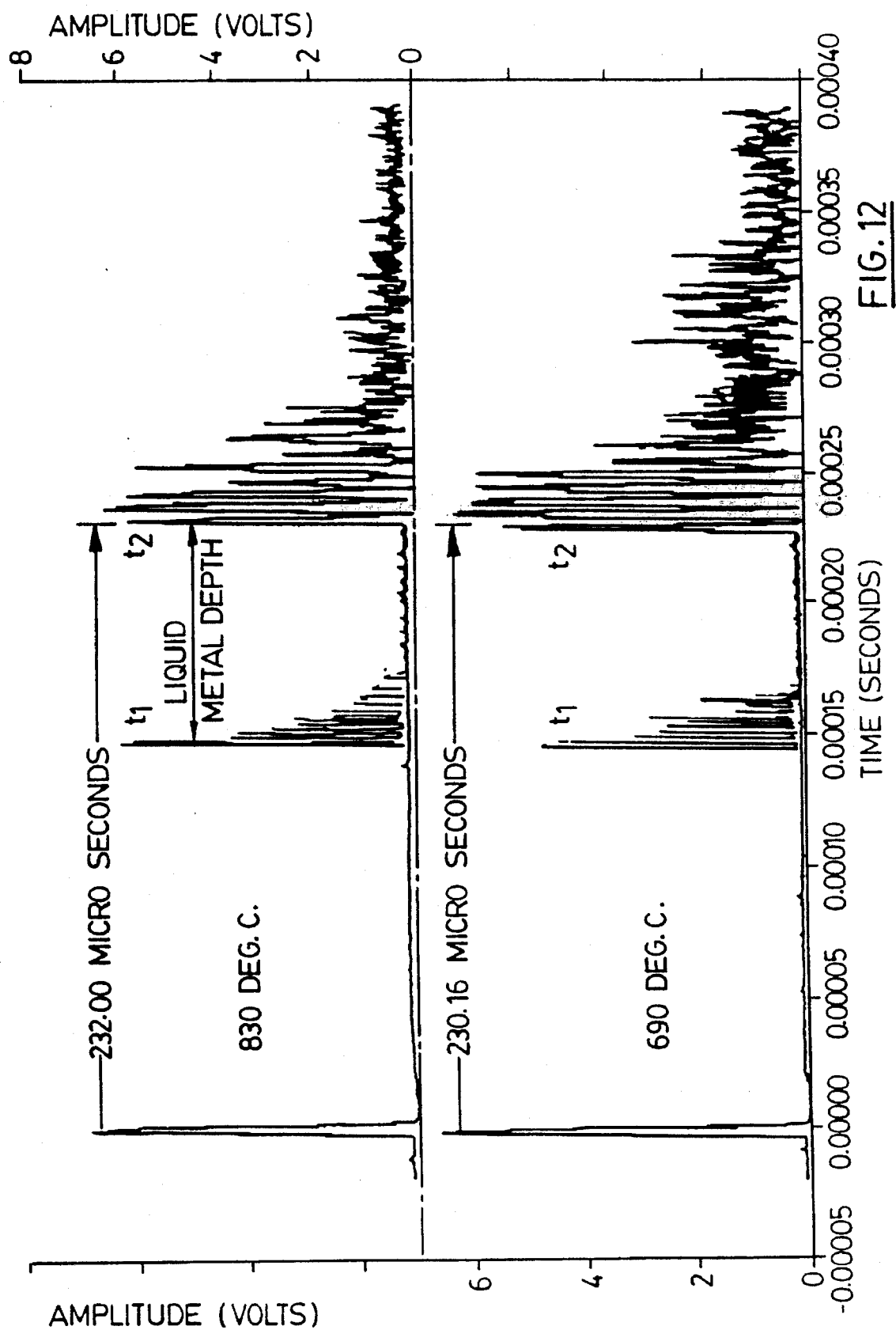
FIG. 12 is another graph relating amplitude to time for the device illustrated in FIGS. 10a and 10b.

The embodiment shown in FIGS. 10 to 12 may be used to measure the position of the metal level in the tundish 100. Sound waves are passed into this liquid metal in the manner already described with the transmitting device shown at 102 held in a final position relative to the tundish 100. At some distance below the metal surface and below the device 102 is held a double reflector 104, the purpose of which is to deflect the sound beam outwards from the first reflector 104a into the liquid metal towards the second reflector 104b which reflects the sound beam up to the liquid metal surface shown at 106.

The sound waves are reflected on a reciprocal path by the metal surface 106 (or for that matter the slag-metal interface). Any change in the surface position will cause this surface 'echo' to move and it can thus be calibrated to depth. It follows that this registered change in depth can be used for metal level control systems.

The reflector 104a is located in a body of graphite/$AlO_2$ bonded material and the outboard reflector 104b is of a similar material and is attached to a lower reflector platform 110. The reflector 104b is spaced some fifteen centimeters from the body so that there is no interference from the body in the upward travel of the sound beam.

The lower reflector platform 110 is supported by two support members 108a, 108b. The transmitting and receiving delay lines, illustrated at 112 and 114 respectively, are aligned at right angles to the support members. In this manner, sound pulses leaving the transmitting delay line are reflected by the reflector 104 and pass beneath the receiving delay line 114. An advantage to this arrangement is that the support members are situated so as not to interfere with the passage of these sound pulses, as would occur for example, if the support members were in line with the transmitting and receiving delay lines. This interference would otherwise be seen as an echo caused by the reflected sound pulse to pass beneath the receiving delay line and thereafter bounce off the adjacent support member and be reflected a second time past the receiving delay line, thereby causing confusion in the measurement. This 'echo' is shown in FIG. 11 entitled 'support reflection'.

Temperature Measurement

By using the instrument in the transmit/receive mode with the second transducer and delay line, such as can be used to measure attenuation (previously described), it will be possible to measure the speed of sound over the distance of travel through the liquid metal. Conventional methods make possible measurements on a time base on the order of nanoseconds. The present technique may be used to register the reflections from the end of the solid delay line at the liquid-solid interface and this will be recorded as time T1. With higher gain, the reflected signal from a reflector placed at a given distance D, there will be another echo registered at time T. The speed of sound in the liquid will now be given by the following formula:

$$V=(T2-T1)/2D$$

as illustrated in FIG. 12.

For any given array involving a liquid phase, and one or two delay lines, the position of the echo from the liquid can be recorded and any change in this will indicate a different time either lower, if the speed of sound increases or higher if the speed of sound decreases. Since the speed of sound shows a linear relationship with temperature, any change in the speed of sound can be related to a change in temperature. Each metal has a coefficient between temperature and the speed of sound.

Figure 13:
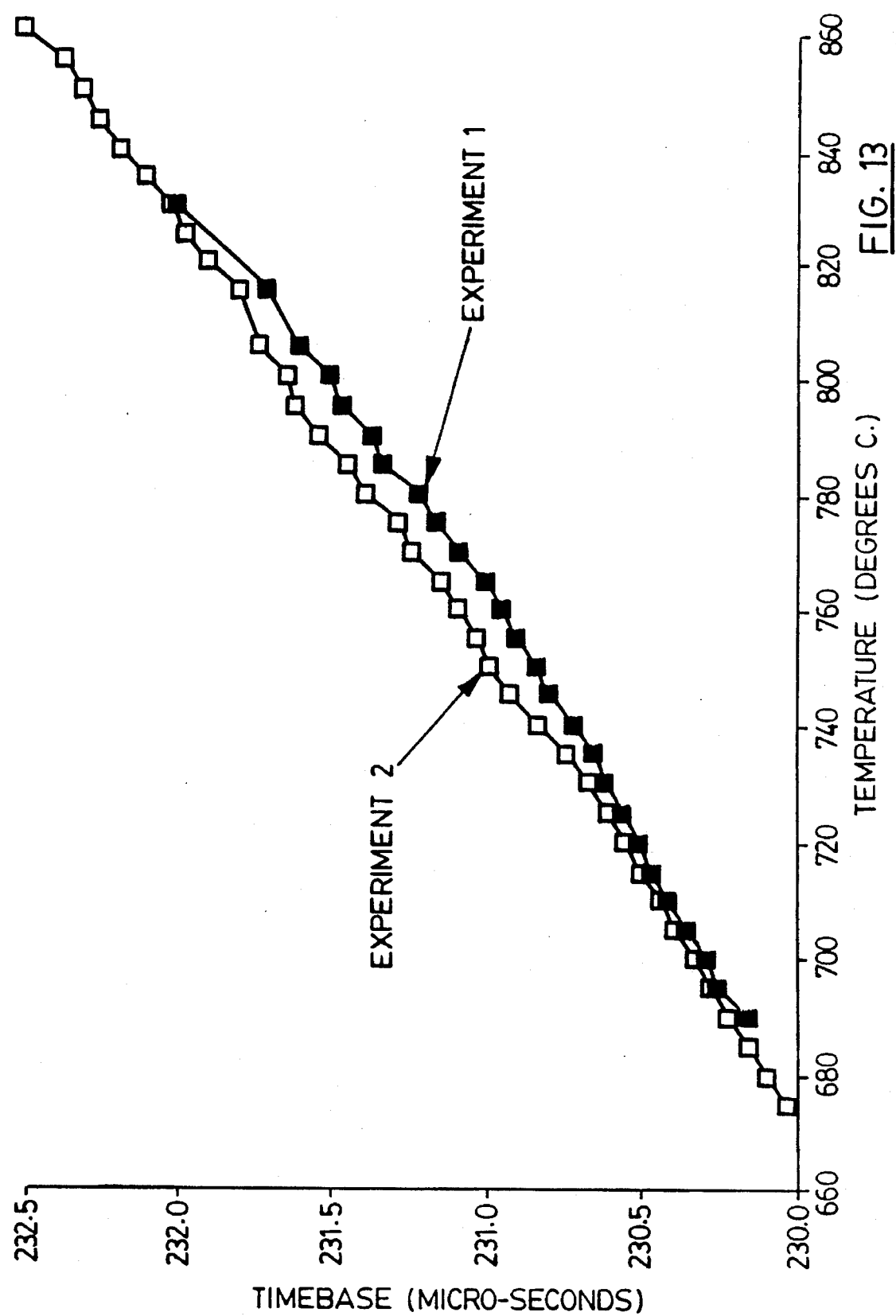
FIG. 13 is a graph relating time to temperature for two experiments with liquid aluminum.

An instrument could be calibrated and a comparative temperature displayed from a datum temperature set by other means, such as double frequency light emission or thermocouple. FIG. 13 illustrates two experiments carded out in this way on liquid aluminum.

The principles used in applying ultrasonic sound for the purposes of examining for metal quality in the liquid condition, and for their treatment can be applied equally to aqueous solutions containing either suspended particles or foreign materials in solution.

Purification of Water and other Liquids

The concept of focusing the sound and counting particles can be achieved but in addition it would be possible, if the examination of the water is to be made in running waters such as rivers or streams to drop suitable reagents ahead of the measuring device (or upstream) such that the reagent will result in a reaction with the dissolved contaminant in a precipitate of particulate material which will then be detected acoustically. This concept could be applied to the control of chemical reactions on a continuous basis. For example chlorine could be detected by using silver nitrate as the reagent. The precipitate of silver chloride can be detected acoustically.

Figure 14:
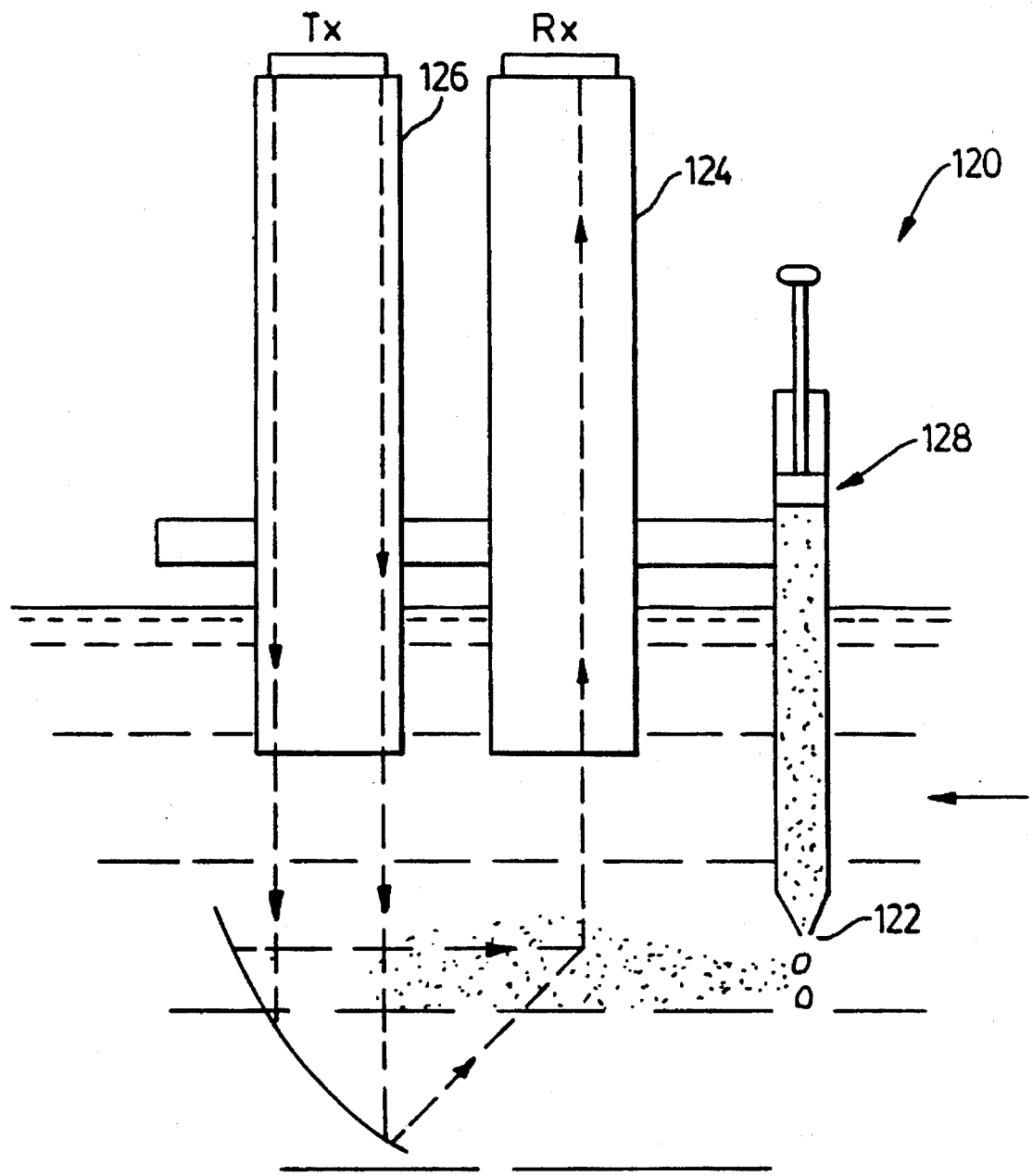
FIG. 14 is a schematic side view of a another ultrasonic detection device.

A device which enables this to occur is shown at 120 in FIG. 14. The device 120 is similar to that shown in FIG. 3b except that device 120 includes a means for depositing a reagent in the liquid upstream of the delay lines. The means has an injection orifice 122 which is positioned in a flow of liquid including foreign material in solution and upstream of the transmitting and receiving delay lines 124, 126. Joined to the orifice 122 is a pump shown schematically at 128 which delivers a known amount of reagent into the solution, that reagent being selected to precipitate the foreign material out of solution.

The above mentioned techniques to interpret the nature of precipitates in solution may be used to determine the nature of the particles making up slurries. In the case, the slurry itself may not be easy to examine because of the concentration of particles. However, a sample of a given amount of the slurry can be transferred to a vessel containing a known amount of water so that the dilutions can be determined by counting the particles and determining their sizes. This technique may be useful in the ceramics industry where by mixing slurries of known particles size distribution, a more compact final material can be obtained.

The counterflow technique for holding back particles will equally apply to water with suspended particles of sewage or similar contaminants.

Cavitation Degassing

Figure 16:
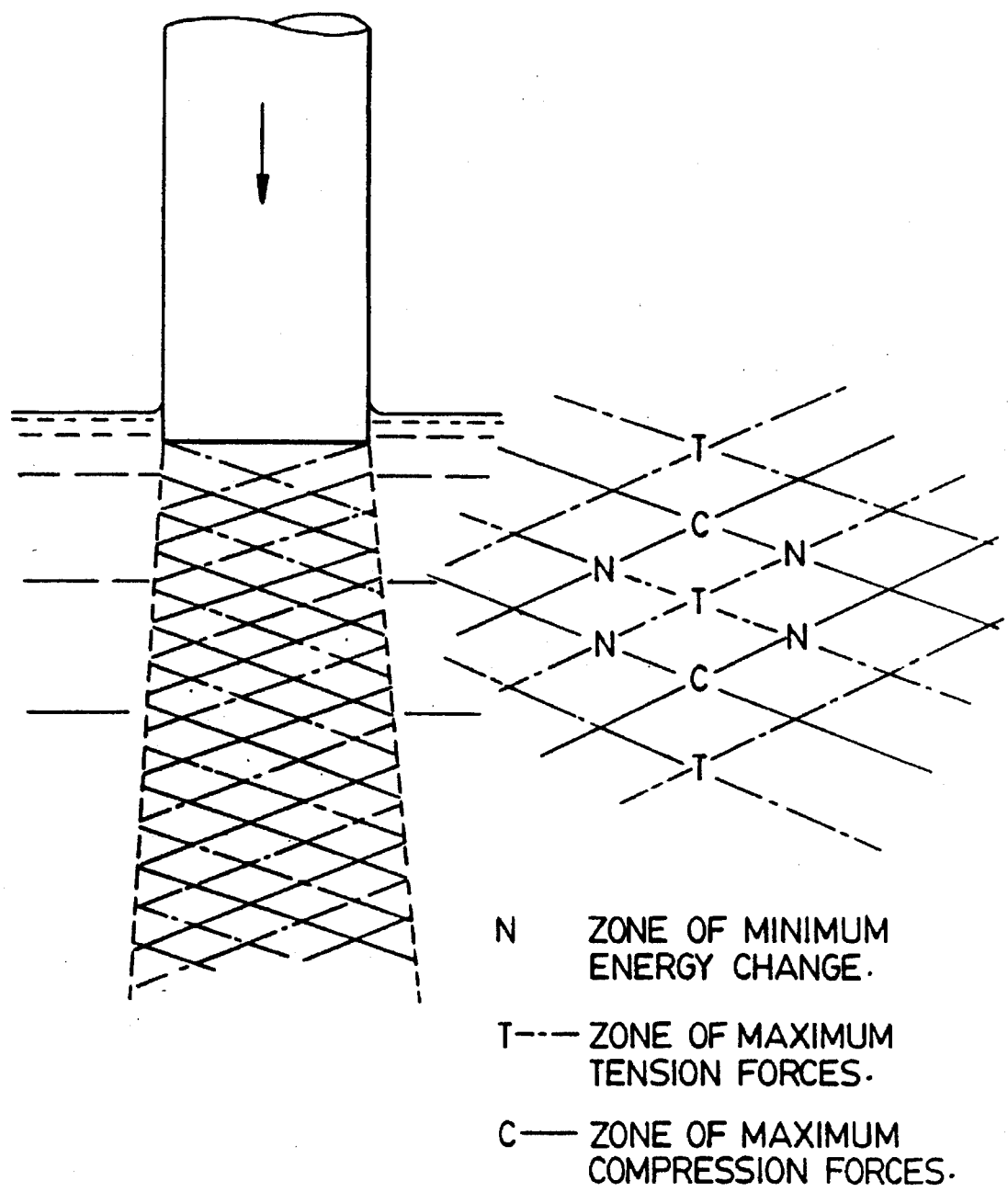
FIG. 16 is a schematic side view of yet another ultrasonic detection device.

Referring to FIG. 16, one of the effects of applying power sound to a liquid metal is that of cavitation, which has been found to occur at points within the sound beam known as 'antinodes'. These zones form a pattern which is related to the dimensions of the sound beam and the frequency used. The zones may be stationary, for example in a situation where the whole system forms a standing wave pattern or they may be moving as a result of factors such as thermal or dimensional variations. The effect of the cavitation is the formation of bubbles in the antinodal zones of extremely low pressure (that is those with maximum tension forces as shown at 'T' in FIG. 16) and into which atomic hydrogen and nitrogen will diffuse. These atomic gases will immediately form a strong molecular bond (thus forming molecular gases) which will inhibit their resolution when the cavitation bubble collapses. However, the bubbles of molecular gases will remain and will agglomerate in the 'N' zones (as shown in FIG. 16), that is the zones of minimum energy change. Thereafter, the bubbles rise to the metal surface due to the buoyancy forces arising from the huge differences in density between gas and metal and thus are removed from the liquid metal.

The system for cleaning metals by the counterflow technique will create this effect. As a result, the liquid metal will be denuded of hydrogen or nitrogen, without the need of expensive vacuum techniques.

In general, the most appropriate materials selected for the delay rod will be that which provides the best acoustic matching, that is the one which provides the minimum acoustic impedance in the expected operating temperature ranges. There may however be exceptions. It may be appropriate to make use of a delay line with a body, a portion of which is to be immersed in a sample and which is formed of a single phase material. That material may be an alloy, at least one constituent of which is common with the sample, thereby to minimize allotriomorphic changes which inhibit sound transmission through the delay line.

For example, liquid Aluminum can be examined using either steel rods or an aluminum alloy itself.

Figure 15:
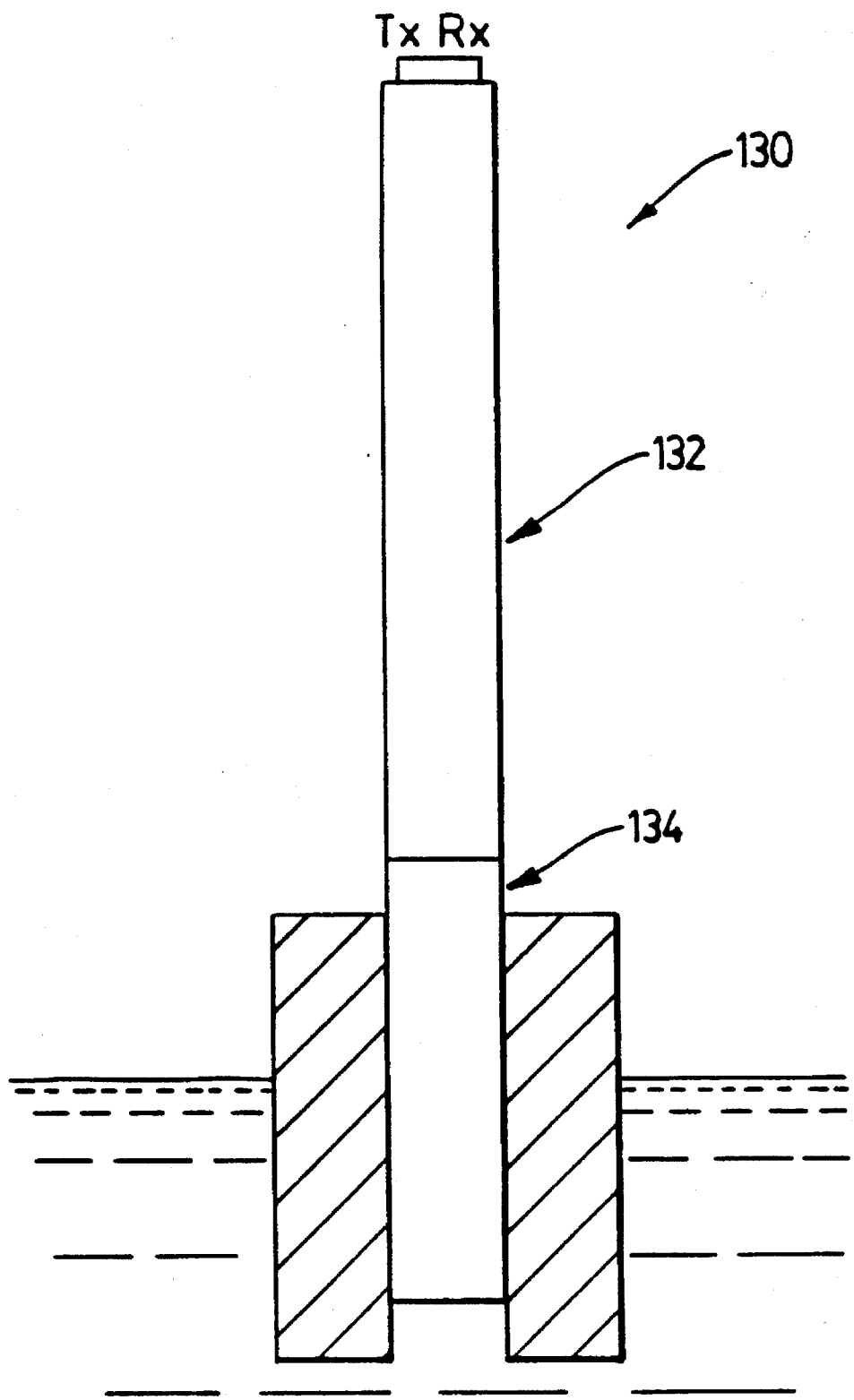
FIG. 15 is a schematic side view of a portion of yet another ultrasonic detection device.

Using steel rods to examine melts may result in considerable losses at the interface, although these losses can be compensated by amplifying the received signals. There may also be more errors in the measurements taken. Liquid steel can be examined by using either a steel rod itself, suitably cooled, or an alloy of steel such as 18-8 stainless. In the case of 18-8 stainless, the acoustic impedance change derived because of the chromium nickel addition will be sufficiently small and should not impose significant losses. This material is in the α condition for the whole range of temperatures up to the melting point. It does not suffer any allotriomorphic changes which inhibit sound transmission. However, one difficulty with using 18-8 stainless steel is the cost. The cost however, can be minimized by using the stainless steel alloy for the sensing region and utilizing mild steel for the remainder of the delay rod, this being done by welding a stainless steel end piece 134 on the mild steel rod 132 as seen in FIG. 15.

Similarly nickel base alloys may be used when examining nickel alloy liquids. Materials which are of a uniform single phase composition but which do not contain elements which will deoxidize the examined alloy, for example silicon, vanadium, titanium or manganese if present in any quantity could be used for example.

The iron chromium alloys could be used providing the composition is held closely in the 15 percent to 20 percent chromium region. Where composite delay lines are used, contamination of the basic melt may occur, although the effects should be insignificant provided the delay line is suitably cooled.

We claim:

1. An ultrasonic detection device comprising an ultrasonic transmitting delay line and an ultrasonic receiving delay line, ultrasonic reflection means placed beyond said transmitting delay line and aligned therewith, said reflection means being dimensioned so that when immersed in a liquid and receiving ultrasonic waves from said transmitting delay line, said reflection means focuses said ultrasonic waves to a focal volume, said receiving delay line receiving reflected ultrasonic waves from extraneous particles in said focal volume allowing for their detection by said receiving delay line.

2. A device as defined in claim 1 wherein said reflection means is in the form of a curved reflector to form a spherical focal volume adjacent said receiving delay line.

3. A device as defined in claim 2 wherein said reflection means is in the form of a reflector shaped to form two inclined planes at an obtuse angle thereby to form a focal volume which is cylindrical in shape adjacent said receiving delay line.

4. A device as defined in claim 2 further comprising an additional reflection means placed below the receiving delay line so that said receiving delay line can be used in a transmit mode to transmit ultrasonic waves into said liquid and in a receive mode to receive reflected ultrasound waves from said additional reflector, said reflected ultrasound waves being representative of a measured total attenuation of said transmitted ultrasound wave.

5. A device as defined in claim 4 wherein said device further comprises computation means arranged to receive an input representative of said reflected ultrasound waves and to generate an output representative of the total quantity of extraneous particles contained in said liquid.

6. A device as defined in claim 4 wherein said device further comprises computation means arranged to receive an input representative of said reflected ultrasound waves and to generate an output representative of the temperature of said liquid.

7. A device as defined in claim 1 further comprising means for depositing a reagent in said liquid upstream of said delay lines.

8. An ultrasonic particle detection device comprising:

an ultrasound transmitting delay line;

an ultrasound receiving delay line;

a reflector aligned with said transmitting delay line to focus ultrasound from said transmitting delay line to a focal volume within a liquid; and a second reflector aligned with said receiving delay line to receive reflected ultrasound waves from extraneous particles in said focal volume and direct said reflected ultrasound to said receiving delay line for detection.

9. A device as defined in claim 8 wherein said transmitting delay line, receiving delay line and first and second reflectors are rotatable about an axis to sweep said focal volume along an arc.

10. A device as defined in claim 9 wherein said first and second reflectors are moveable along an axis parallel to said axis of rotation.

11. A device as defined in claim 10 further including a third reflector positioned between said first and second reflectors, said third reflector directing ultrasound from said transmitting delay line directly to said receiving delay line to allow an attenuation measurement of said liquid to be made.

* * * * *